United States Patent
Ho et al.

(10) Patent No.: US 8,327,848 B2
(45) Date of Patent: Dec. 11, 2012

(54) PRESSURE REDUCING VALVE

(75) Inventors: Peter Chi Fai Ho, Pittsburgh, PA (US);
Zachary D. Paul, Pittsburgh, PA (US);
Lance Busch, Trafford, PA (US);
Richard Andrew Sofranko, Finleyville, PA (US); Marcel D. Jaffre, Greensburg, PA (US)

(73) Assignee: RIC Investments, LLC, Wilmington, DE (US)

( * ) Notice: Subject to any disclaimer, the term of this patent is extended or adjusted under 35 U.S.C. 154(b) by 1377 days.

(21) Appl. No.: 11/860,184

(22) Filed: Sep. 24, 2007

(65) Prior Publication Data
US 2008/0078395 A1 Apr. 3, 2008

Related U.S. Application Data

(60) Provisional application No. 60/847,825, filed on Sep. 28, 2006.

(51) Int. Cl.
*A62B 9/02* (2006.01)
*A61M 16/00* (2006.01)

(52) U.S. Cl. ......... 128/205.24; 128/204.18; 128/204.26; 128/200.24

(58) Field of Classification Search ............. 128/200.24, 128/201.28, 202.28, 202.29, 203.11, 205.24, 128/207.12; 137/512, 512.1, 512.3, 512.15, 137/513.3, 601.2, 625, 855, 908, 102, 484.2; 251/65, 336, 12, 142, 149, 175, 176, 180, 251/283, 313, 321, 337
See application file for complete search history.

(56) References Cited

U.S. PATENT DOCUMENTS

| | | | |
|---|---|---|---|
| 2,610,859 A * | 9/1952 | Wilcox et al. | 137/102 |
| 5,002,050 A | 3/1991 | McGinnis | |
| 5,163,424 A | 11/1992 | Køhnke | |
| 5,398,673 A * | 3/1995 | Lambert | 128/202.28 |
| 5,584,288 A * | 12/1996 | Baldwin | 128/202.28 |
| 5,813,401 A | 9/1998 | Radcliff et al. | |
| 5,878,743 A | 3/1999 | Zdrojkowski et al. | |
| 5,896,857 A | 4/1999 | Hely et al. | |
| 6,105,575 A | 8/2000 | Estes et al. | |
| 6,189,532 B1 * | 2/2001 | Hely et al. | 128/205.24 |
| 6,196,252 B1 * | 3/2001 | Martin et al. | 137/102 |
| 6,615,831 B1 * | 9/2003 | Tuitt et al. | 128/204.18 |
| 6,766,800 B2 | 7/2004 | Murdock et al. | |
| 6,792,965 B2 * | 9/2004 | Kunkler | 137/113 |
| 7,063,086 B2 | 6/2006 | Shahbazpour et al. | |
| 7,089,939 B2 * | 8/2006 | Walker et al. | 128/205.24 |
| 7,174,893 B2 * | 2/2007 | Walker et al. | 128/206.21 |
| 7,565,906 B2 * | 7/2009 | Arcilla et al. | 128/204.19 |
| 7,637,279 B2 * | 12/2009 | Amley et al. | 137/102 |
| 2004/0211422 A1 | 10/2004 | Arcilla et al. | |
| 2005/0245837 A1 | 11/2005 | Pougatchev et al. | |

* cited by examiner

*Primary Examiner* — Annette Dixon
(74) *Attorney, Agent, or Firm* — Michael W. Haas

(57) ABSTRACT

A pressure reducing valve for use in a system adapted to deliver a breathing gas to a patient. The pressure reducing valve is structured to communicate a flow of breathing gas to such a patient's airway during an inspiratory phase. The pressure reducing valve is structured to isolate the flow of breathing gas from the patient's airway and to "dump" the flow of breathing gas and a flow of exhalation gas to atmosphere during the expiratory phase. The flow of breathing gas is dumped to atmosphere through a first number of ports; whereas a flow of exhalation gas is dumped to atmosphere through a second number of ports. Because the flow of breathing gas remains isolated from the flow of exhalation gas, less effort is required by a patient during the expiratory phase.

28 Claims, 19 Drawing Sheets

PRESSURE REDUCING VALVE

CROSS-REFERENCE TO RELATED APPLICATIONS

This application claims priority under 35 U.S.C. §119(e) from provisional U.S. patent application No. 60/847,825 filed Sep. 28, 2006 the contents of which are incorporated herein by reference.

BACKGROUND OF THE INVENTION

1. Field of the Invention

The present invention pertains to the delivery of a flow of breathing gas to the airway of a patient and more particularly to an apparatus and method for providing improved comfort for a patient receiving a flow of breathing gas.

2. Description of the Related Art

There are numerous situations where it is necessary or desirable to deliver a flow of breathing gas to the airway of a patient. For example, it is known to deliver a flow of breathing gas to a patient during at least a portion of the breathing cycle to treat breathing and/or cardiac disorders such as obstructive sleep apnea syndrome, chronic obstructive pulmonary disease, congestive heart failure, and other respiratory and/or breathing disorders.

While sleeping, a patient suffering from obstructive sleep apnea syndrome (OSAS) is prone to having their airway narrow and/or collapse due to, for instance, mechanical collapsing forces that result from the structure of the airway tissues, muscle tone, and body position. One method of treating OSAS is continuous positive airway pressure (CPAP) therapy. With CPAP therapy, a flow of gas is supplied at a constant pressure of sufficient magnitude to splint the patient's airway open and to prevent narrowing and/or collapse of the airway.

During a normal breathing cycle, however, the pressure gradient between the lungs and the exterior of the body is not constant. For example during inspiration, the pressure gradient (sometimes referred to as the "inspiratory pressure gradient") falls from zero at the start of inspiration to a peak negative value and then rises back to zero at the end of inspiration. During expiration, the pressure gradient (sometimes referred to as the "expiratory pressure gradient") rises from zero at the start of expiration to a peak value and then falls back to zero as expiration ends. Because the pressure gradient varies over the breathing cycle, the pressure necessary to overcome airway collapse should ideally vary over the breathing cycle. Thus, although CPAP provides a simple treatment solution for OSAS, the application of a constant splinting pressure to the airway exposes the patient to pressures that are higher than the pressures needed to support the airway for most of the breathing cycle.

Advanced therapies, such as bi-level positive airway pressure (bi-level PAP) therapies and proportional positive airway pressure therapies, seek to take advantage of the different pressure requirements to lower the pressure at certain instances during the breathing cycle. In bi-level PAP therapy, for example, a flow of gas is supplied to a patient's airway at a first pressure during inhalation and a flow of gas at a lower pressure is supplied to the patient's airway during exhalation. These advanced therapies, however, may cause discomfort because the patient still must overcome the resistance created by the low pressure flow of gas supplied during exhalation.

Accordingly, a need exists for an apparatus and method for providing improved comfort for a patient receiving a flow of breathing gas which overcomes these and other problems associated with known systems.

SUMMARY OF THE INVENTION

In accordance with an aspect of the present invention, a pressure reducing valve comprises a valve body and an inner sleeve. The valve body has a number of pressurized gas exhaust ports and a number of exhalation gas exhaust ports. The inner sleeve has a number of inner ports. The inner sleeve is movable within the valve body between a closed position in which the inner ports are closed and the pressurized gas exhaust ports and the exhalation gas exhaust ports are open and an open position in which the inner ports are open and the pressurized gas exhaust ports and the exhalation gas exhaust ports are closed.

According to another aspect of the present invention, a pressure reducing valve comprises a valve body and an inner sleeve. The valve body has a patient interface end and a pressure generator end with at least two exhaust ports therebetween. The inner sleeve is movable within the valve body. The inner sleeve is structured to communicate a flow of positive pressure gas from the pressure generator end to the patient interface end during an inspiratory phase and is structured to divert the flow of positive pressure gas to a first one of the at least two exhaust ports during an expiratory phase.

According to another aspect of the present invention, a method for providing a breathing gas to a patient comprises communicating the breathing gas through a patient circuit to an airway of such a patient during an inspiratory phase, wherein the patient circuit has at least a breathing gas exhaust port and an exhalation gas exhaust port, diverting the breathing gas away from the airway of such a patient through the breathing gas exhaust port during an expiratory phase, and directing an exhalation gas from the airway of such a patient through the exhalation exhaust port during the expiratory phase.

According to another aspect of the present invention, in a system adapted to provide a regimen of respiratory therapy to a patient by providing a flow of breathing gas via a patient circuit including a pressure reducing valve with a first exhaust port and a second exhaust port therein, a method comprises delivering the flow of breathing gas to the airway of such a patient through the patient circuit during an inspiratory phase and diverting the flow of breathing gas away from the airway of such a patient through the first exhaust port while disposing of a flow of exhalation gas from the airway of such a patient through the second exhaust port during an expiratory phase.

According to another aspect of the present invention, an apparatus for delivering a flow of positive pressure gas to an airway of a patient comprises a gas flow generator structured to produce the flow of positive pressure gas, a patient interface device structured to communicate the flow of positive pressure gas to the airway of such a patient, and a patient circuit structured to couple the gas flow generator to the patient interface device, wherein the patient circuit includes a pressure reducing valve with a valve body and an inner sleeve, wherein the valve body has at least two exhaust ports therein, wherein the inner sleeve is movable within the valve body, wherein the inner sleeve is structured to communicate the flow of positive pressure gas from the gas flow generator to the patient interface device during an inspiratory phase, and wherein the inner sleeve is structured to divert the flow of positive pressure gas to a first one of the at least two exhaust ports during an expiratory phase.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
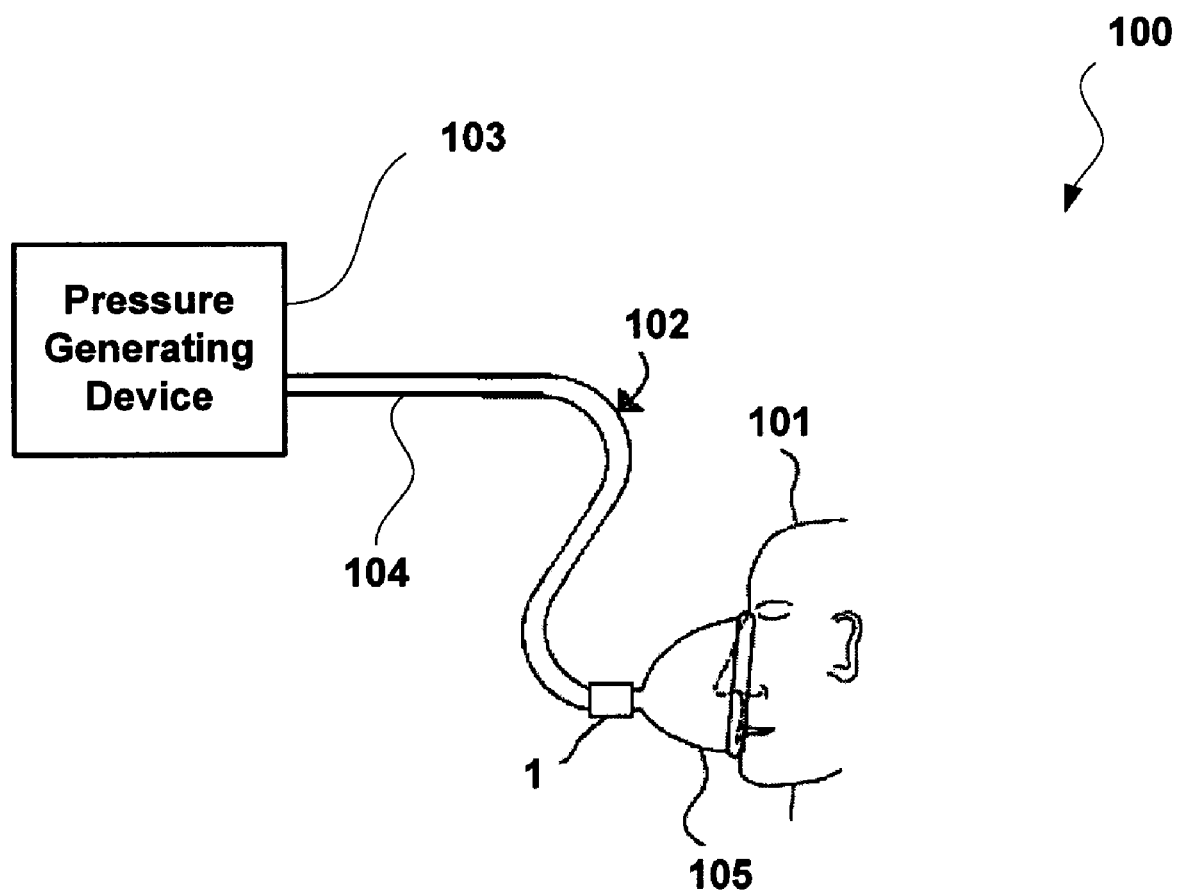
FIG. 1 is a schematic view of a system adapted to provide a regimen of respiratory therapy according to one embodiment of the present invention.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

A system 100 adapted to provide a regimen of respiratory therapy to a patient 101 according to one embodiment is generally shown in FIG. 1. System 100 includes a pressure generating device 103, a patient circuit 102, and a patient interface device 105. Pressure generating device 103 is structured to generate a flow of breathing gas and may include, without limitation, ventilators, pressure support devices (such as a continuous positive airway pressure device, or CPAP device), variable pressure devices (e.g., BiPAP®, Bi-Flex®, or C-Flex™ devices manufactured and distributed by Respironics, Inc. of Murrysville, Pa.), and auto-titration pressure support systems.

Patient circuit 102 is structured to communicate the flow of breathing gas from pressure generating device 103 to patient interface device 105. In the current embodiment, patient circuit 102 includes a conduit 104 and a pressure reducing valve 1 which, as will be discussed in more detail herein, is adapted to provide a pressure reduction effect at certain instances during the breathing cycle.

Patient interface 105 is typically a nasal or nasal/oral mask structured to be placed on and/or over the face of patient 101. Any type of patient interface device 105, however, which facilitates the delivery of the flow of breathing gas communicated from pressure generating device 103 to the airway of patient 101 may be used while remaining within the scope of the present invention. As shown in FIG. 1, patient interface 105 is coupled directly with pressure reducing valve 1; other arrangements, however, are contemplated.

FIGS. 2-11, 20, and 21 illustrate various embodiments of a pressure reducing valve for use with a system adapted to provide a regimen of respiratory therapy to a patient, such as and without limitation, system 100. In each embodiment, the pressure reducing valve is structured to isolate the patient's airway from the flow of breathing gas by "dumping" the flow of breathing gas to atmosphere during the expiratory phase. The pressure reducing valve is also structured to dump a flow of exhalation gas to atmosphere with minimal or no mixing of the flow of breathing gas and the flow of exhalation gas. For example, the flow of breathing gas is dumped to atmosphere through a first number of ports; whereas a flow of exhalation gas is dumped to atmosphere through a second number of ports. Because the flow of breathing gas remains substantially isolated from the flow of exhalation gas, less effort is required by patient 101 during the expiratory phase.

In effect, the pressure reducing valves of the present invention are structured to mechanically change a continuous pressure flow of gas (e.g., a flow of gas from a CPAP device) to a variable pressure flow of gas (e.g., a flow of gas from a bi-level and/or a C-FLEX™ device). Current bi-level devices do not respond well at low supply pressures. For example at low pressures, current bi-level devices produce an expiratory positive air pressure (EPAP) that is equal to the inspiratory positive air pressure (IPAP). It should be noted that the pressure reducing valves of the present invention, however, can convert the continuous pressure flow of gas to the variable pressure flow of gas over a full range of supply pressures. For example, a pressure reducing valve of the present invention can convert flow of gas supplied by a CPAP device to a variable pressure flow of gas even at low pressures. With the pressure reducing valve, EPAP is always lower than IPAP when the valve is in the closed position.

Figure 2:
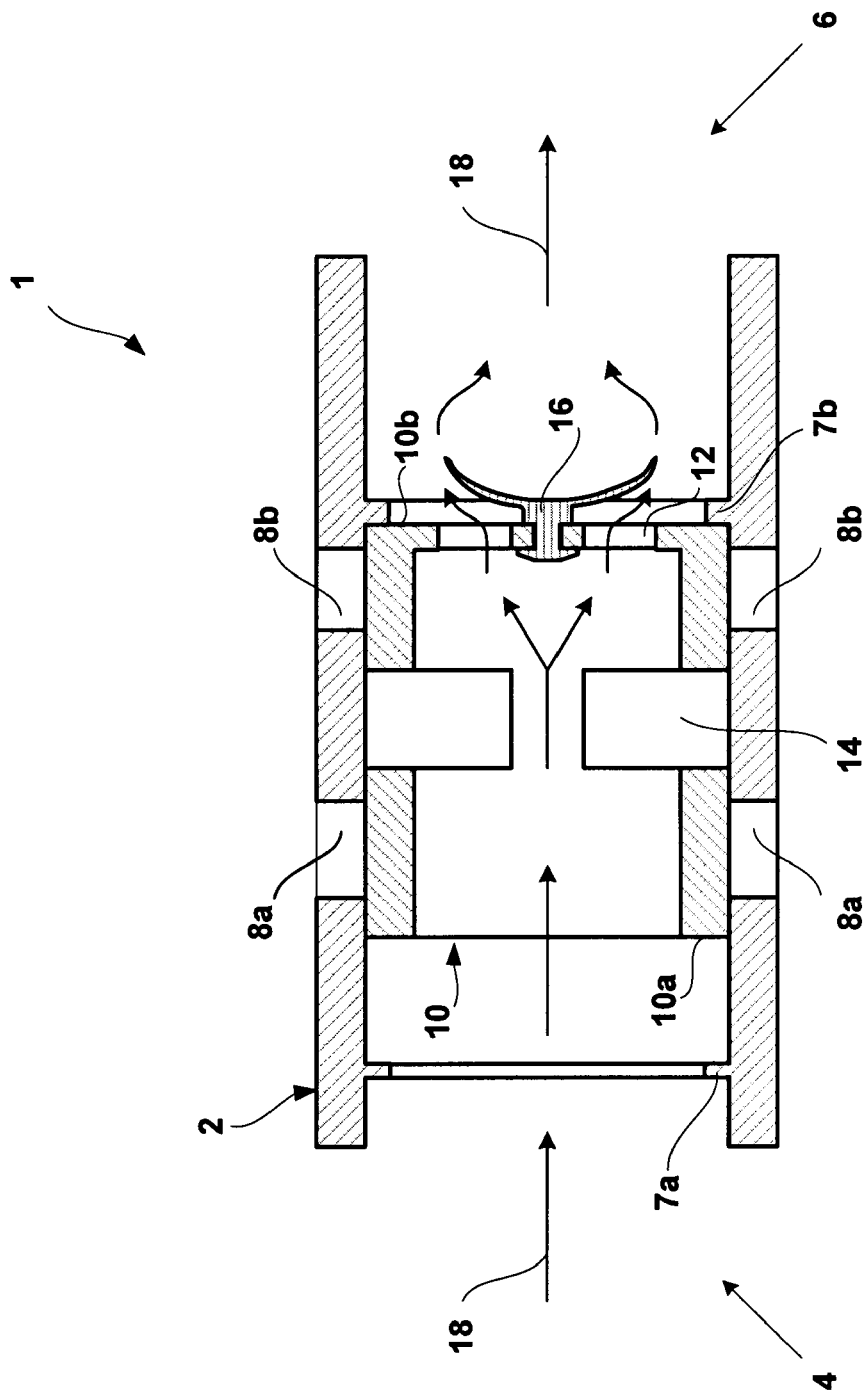
FIG. 2 is a schematic view of a pressure reducing valve illustrated in an open position according to one embodiment of the present invention.
Figure 3:
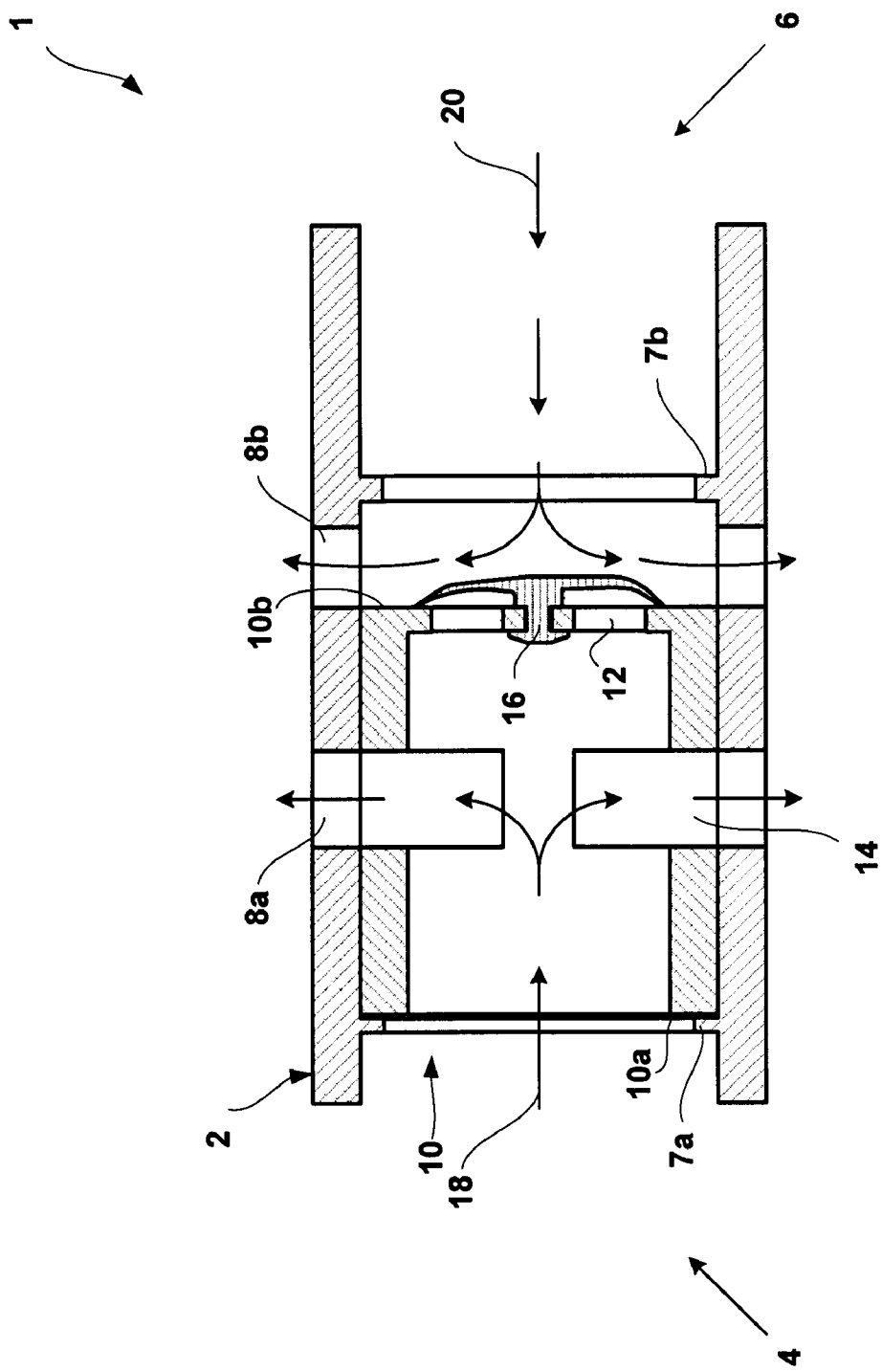
FIG. 3 illustrates the pressure reducing valve of FIG. 2 in a closed position.

Referring now to FIGS. 2 and 3, a pressure reducing valve 1 according to one embodiment of the present invention is illustrated. Pressure reducing valve 1 includes a valve body 2 and an inner sleeve 10. Valve body 2 has a pressure generator end 4 and a patient interface end 6. Pressure generator end 4 is structured to receive a flow of positive pressure gas (i.e., breathing gas; indicated by arrow 18, for example, in FIG. 2) from a pressure generating device. For example, pressure generator end 4 is adapted to couple with one end of conduit 104 (FIG. 1); the other end of conduit 104 is adapted to couple with pressure generating device 103. Patient interface end 6 is structured to deliver the flow of positive pressure gas 18 to the airway of a patient and/or to receive a flow of exhalation gas (as indicated by arrow 20, for example, in FIG. 3) from the airway of the patient. For example, patient interface end 6 is adapted to couple with patient interface device 105 (FIG. 1) which is in fluid communication with the airway of patient 101.

Valve body 2 includes a number of pressurized gas exhaust ports 8a and a number of exhalation gas exhaust ports 8b extending through the wall thereof. As will be discussed in more detail below, pressurized gas exhaust ports 8a and exhalation gas exhaust ports 8b are structured to allow flow of positive pressure gas 18 and flow of exhalation gas 20, respectively, to be communicated through valve body 2. Flow of positive pressure gas 18 typically has a greater volume than flow of exhalation gas 20. Accordingly, pressurized gas exhaust ports 8a are generally larger than exhalation gas exhaust ports 8b in the current embodiment. As seen in FIGS. 2-3, valve body 2 also includes a first stop ring 7a and a second stop ring 7b, each of which is structured to limit the amount of travel available to inner sleeve 10 within valve body 2.

Inner sleeve 10 includes a number of inner ports 12 and a number of orifices 14. A sealing member 16 (such as, without limitation, an umbrella valve, a diaphragm valve, a butterfly valve, a duck-bill valve, a cone valve, a spiral valve, and a bi-leaflet valve) is structured to control flow of positive pressure gas 18 through inner ports 12. In the embodiment shown in FIGS. 2-3, an umbrella valve 16 is employed as the sealing member. Inner sleeve 10 is received within valve body 2 and is movable therein (for example, between first stop ring 7a and second stop ring 7b). In the current embodiment, a clearance of approximately 0.05 inches between inner sleeve 10 and valve body 2 is employed to insure adequate freedom of movement; however, other clearance amounts are contemplated. Additionally, surfaces of valve body 2 and/or surfaces of inner sleeve 10 which come into contact with each other may be coated with polytetrafluoroethylene (PTFE), or another suitable material, to reduce friction and improve wear resistance.

In the current embodiment, valve body 2 and inner sleeve 10 are constructed of a plastic material. However, it is contemplated that valve body 2 and/or inner sleeve 10 may be constructed from another material. Inner sleeve 10, for example, may be constructed of a metal such as, without limitation, titanium or aluminum.

As employed herein, pressure reducing valve 1 is said to be "open" or in an "open position" when inner ports 12 are substantially open (i.e., when sealing member 16 does not substantially occlude inner ports 12) and pressurized gas exhaust ports 8a and exhalation gas exhaust ports 8b are substantially closed (i.e., when inner sleeve 10 substantially occludes exhaust ports 8a and 8b). Pressure reducing valve 1 is typically in the open position during an inspiratory phase (i.e., when a patient is inhaling).

Referring to FIG. 2, the radial surface at the end of inner sleeve 10 nearest pressure generator end 4 may be referred to as a "pressure generator impingement face" 10a. Additionally, the radial surface at the end of inner sleeve 10 nearest patient interface end 6 may be referred to as a "patient interface impingement face" 10b. Flow of positive pressure gas 18 exerts a force on pressure generator impingement face 10a causing inner sleeve 10 to move within valve body 2. Typically, this movement continues until patient interface impingement face 10b contacts second sealing ring 7b. Flow of positive pressure gas 18 also causes umbrella valve member 16 to flex such that inner ports 12 are substantially open. In the open position, flow of positive pressure gas 18 is communicated from the pressure generator end 4 to the patient interface end 6 through inner ports 12. Flow of positive pressure gas 18, however, is isolated from pressurized gas exhaust ports 8a and exhalation gas exhaust ports 8b by inner sleeve 10.

As employed herein, pressure reducing valve 1 is said to be "closed" or in a "closed position" when inner ports 12 are substantially closed (i.e., when sealing member 16 substantially occludes inner ports 12) and pressurized gas exhaust ports 8a and exhalation gas exhaust ports 8b are substantially open (i.e., when inner sleeve 10 does not substantially occlude exhaust ports 8a and 8b). Pressure reducing valve 1 is typically in the closed position during an expiratory phase (i.e., when a patient is exhaling). Referring to FIG. 3, for example, flow of exhalation gas 20 exerts a force on patient interface impingement face 10b causing inner sleeve 10 to move within valve body 2. Typically this movement continues until pressure generator impingement face 10a contacts first sealing ring 7a. Flow of exhalation gas 20 also causes umbrella valve 16 to flex such that inner ports 12 are closed (i.e., flow of positive pressure gas 18 and/or flow of exhalation gas 20 through inner ports 12 is hindered). In the closed position, flow of positive pressure gas 18 is diverted, through orifices 14, to pressurized gas exhaust ports 8a, and out to atmosphere. Additionally, flow of exhalation gas 20 is expelled to atmosphere through exhalation gas exhaust ports 8b. In the closed position, flow of positive pressure gas 18 is not communicated from pressure generator end 4 to patient interface end 6 through inner ports 12.

As seen in FIG. 3, flow of exhalation gas 20 does not mix with, and is not impeded by, flow of positive pressure gas 18 when pressure reducing valve 1 is in the closed position. Accordingly, the amount of work required of the patient to overcome the resistance caused by flow of positive pressure gas 18 during the expiratory phase is significantly reduced and/or eliminated. It should be noted that a negligible amount of mixing, due to leakage associated with sealing member 16 and/or between inner sleeve 10 and valve body 2, is permissible.

Figure 4:
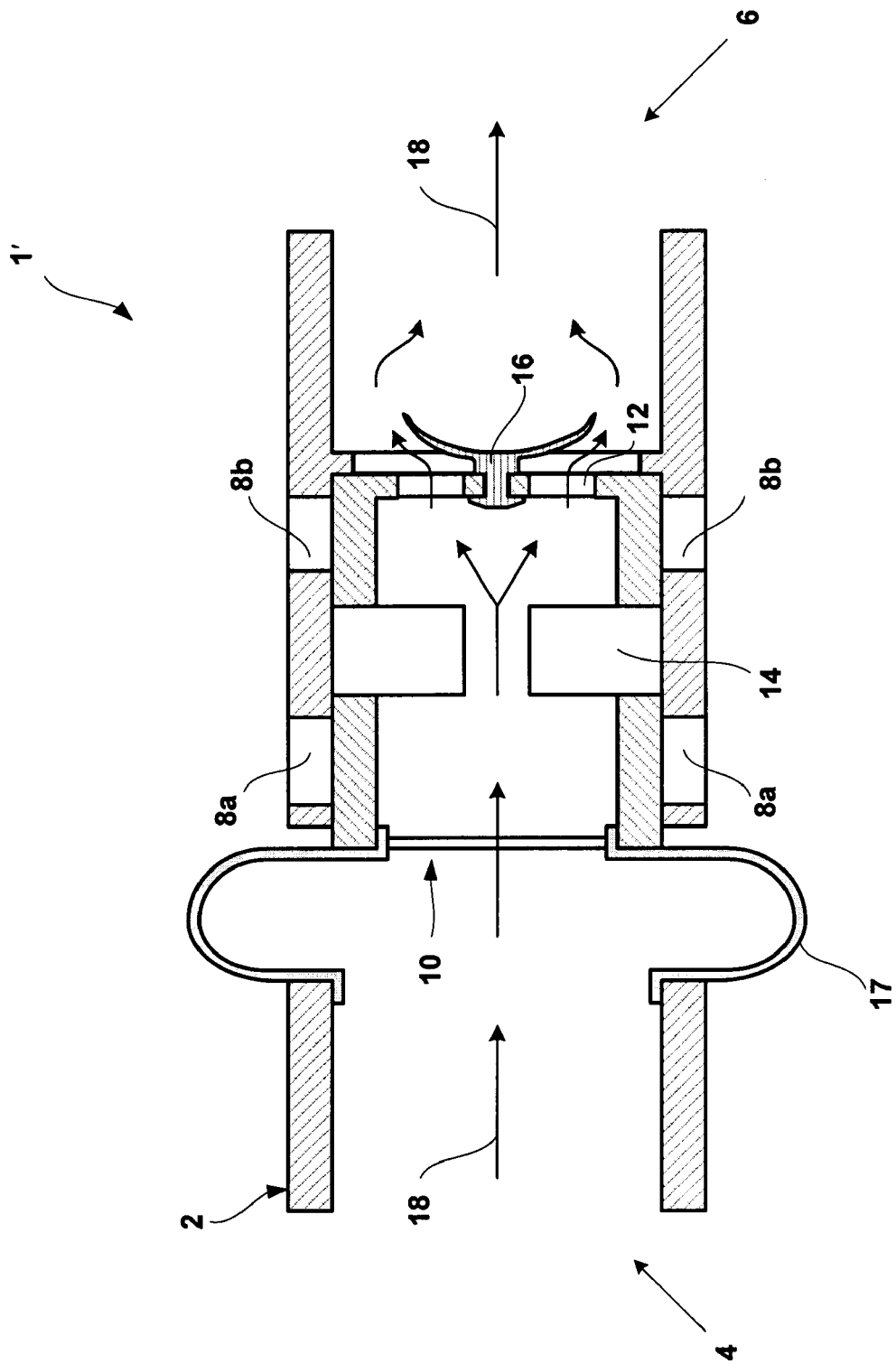
FIG. 4 is a schematic view of a pressure reducing valve illustrated in an open position according to another embodiment of the present invention.
Figure 5:
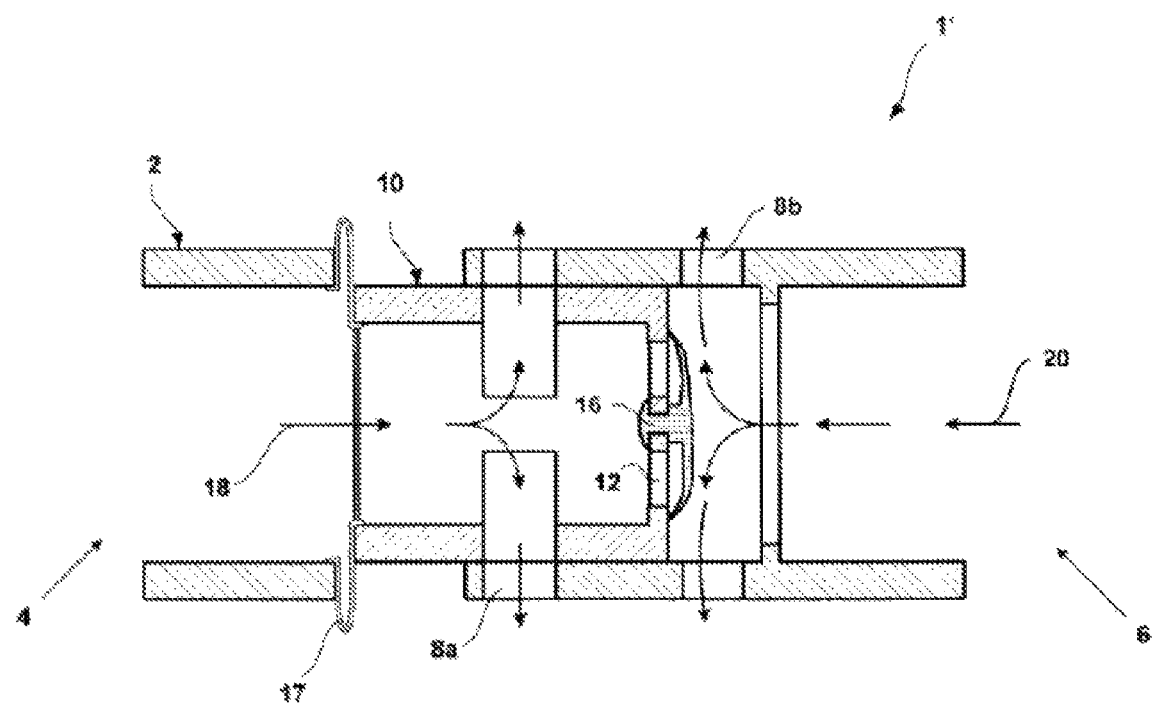
FIG. 5 illustrates the pressure reducing valve of FIG. 4 in a closed position.
Figure 6:
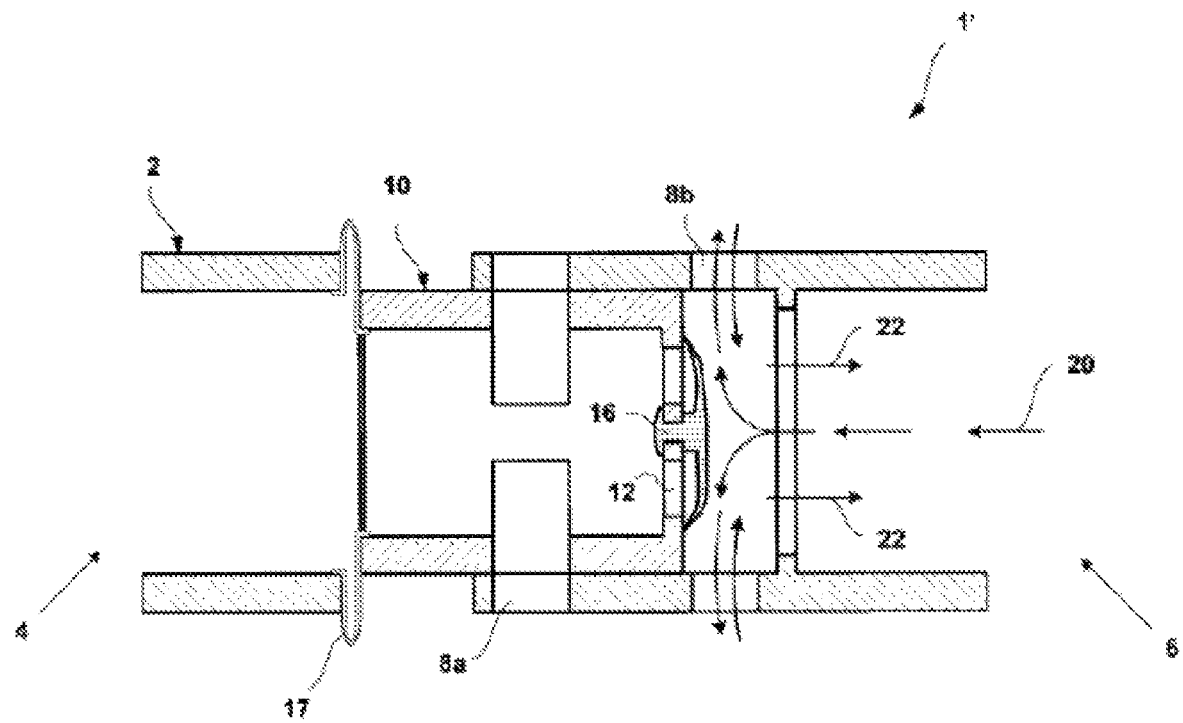
FIG. 6 illustrates the pressure reducing valve of FIG. 4 in the closed position when a flow of positive pressure gas is absent therefrom.

A pressure reducing valve 1' according to another embodiment of the present invention is illustrated in FIGS. 4-6. FIG. 4 illustrates pressure reducing valve 1' in the open position. FIG. 5 illustrates pressure reducing valve 1' in the closed position. Pressure reducing valve 1' functions in a manner similar to that discussed above in conjunction with FIGS. 2-3 for pressure reducing valve 1.

Pressure reducing valve 1' also includes a biasing member 17. In the current embodiment, biasing member 17 is a bellows structured to reposition inner sleeve 10 in the closed position when, for example, flow of positive pressure gas 18 is absent from the pressure generator end 4 (such as when power is removed from pressure generating device 103). Accordingly, pressure reducing valve 1' functions as an entrainment valve when flow of positive pressure gas 18 is absent.

Referring to FIG. 6, for example, bellows 17 returns inner sleeve 10 to the closed position such that flow of exhalation gas 20 is directed to atmosphere and a flow of non-pressurized inhalation gas 22 is communicated to the patient's airway. Although a bellows is employed as biasing member 17 in FIGS. 4-6, it is contemplated that other biasing members (such as, without limitation: a spring, a magnets, etc.) may be used while remaining within the current embodiment.

Figure 20:
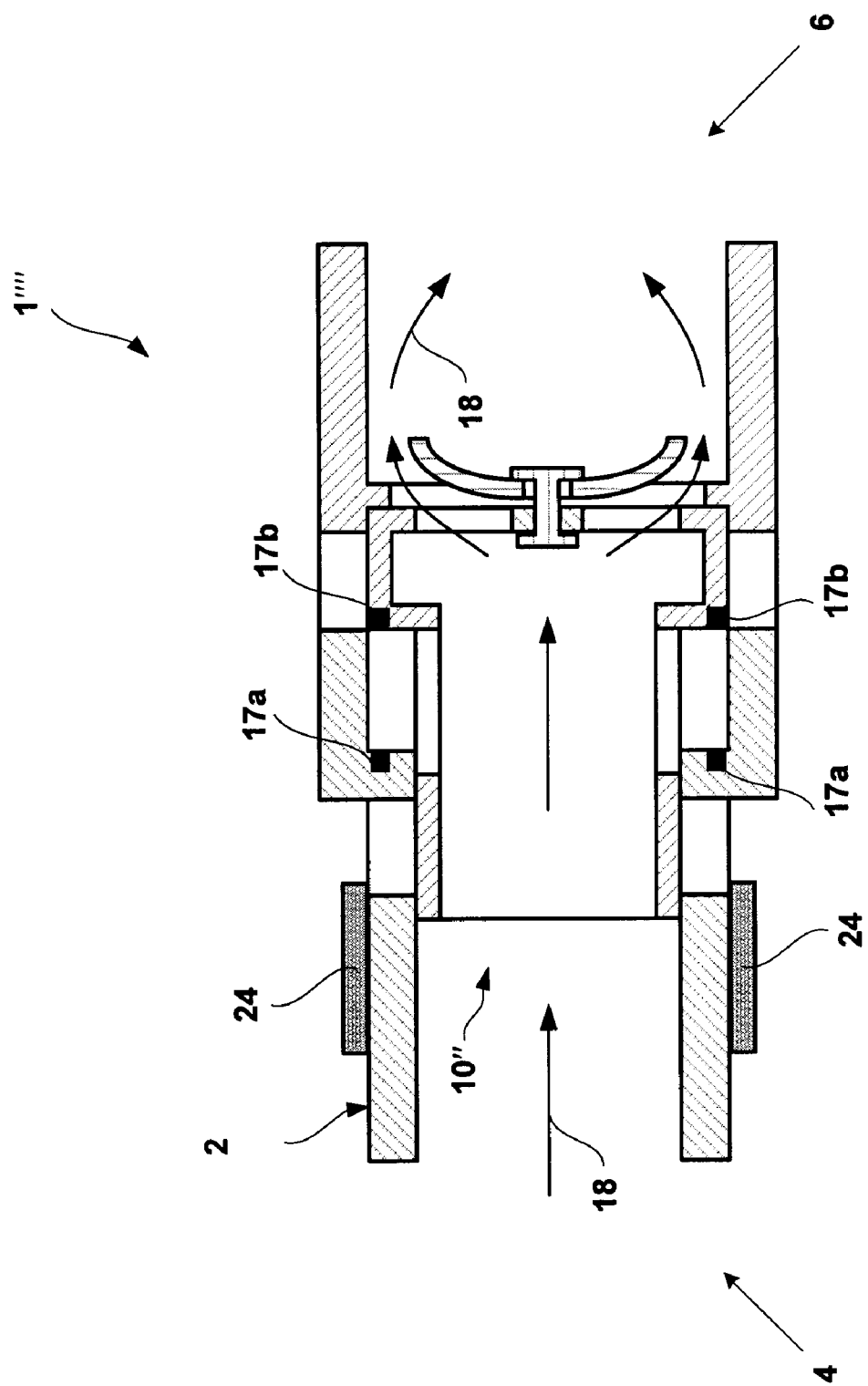
FIG. 20 is a schematic view of a pressure reducing valve illustrated in an open position according to another embodiment of the present invention.
Figure 21:
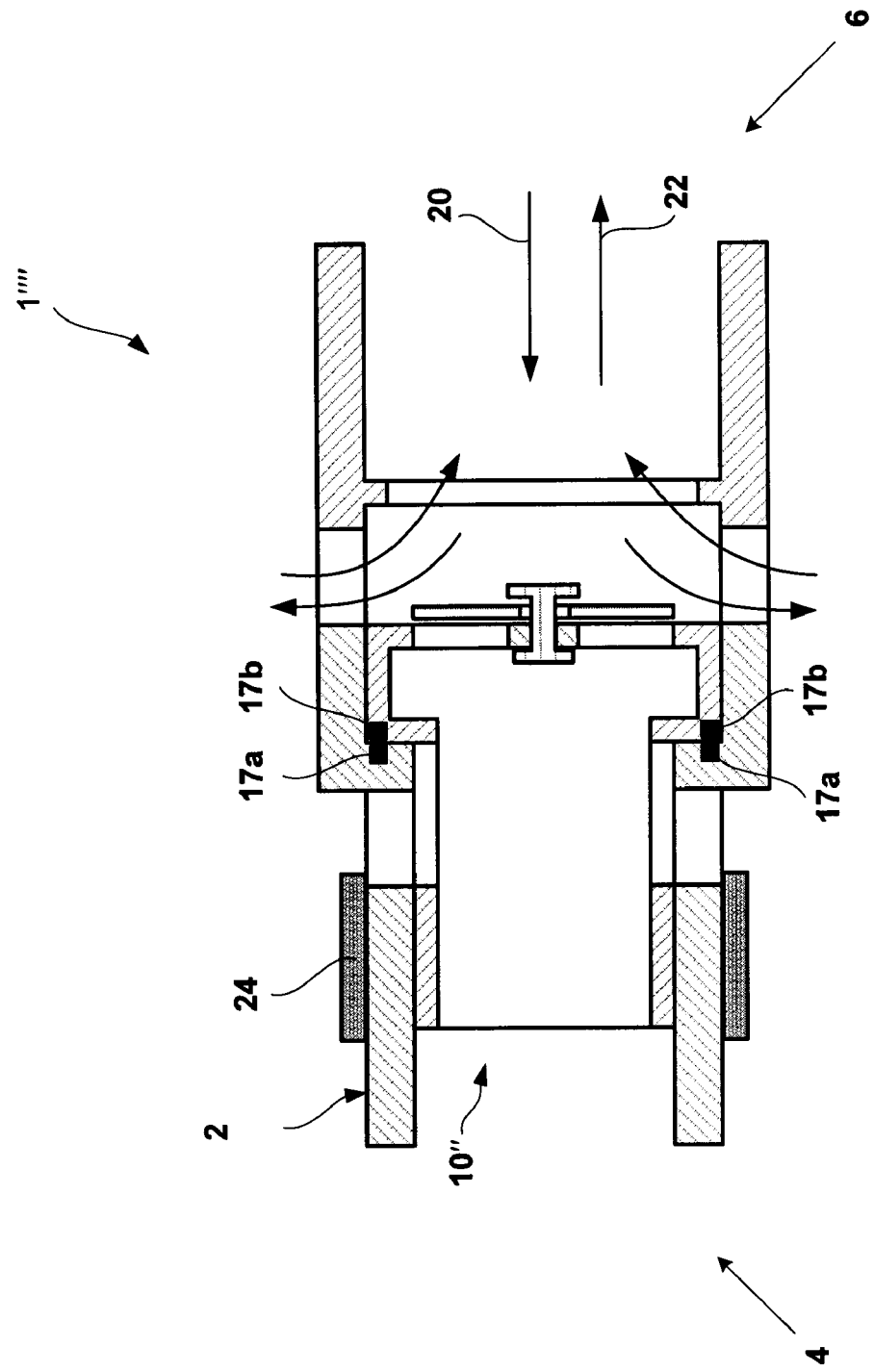
FIG. 21 illustrates the pressure reducing valve of FIG. 20 in a closed position with a flow of positive pressure gas absent therefrom.

FIGS. 20-21, for example, show pressure reducing valve 1'''' employing magnets (17a, 17b) as the biasing member 17. When flow of positive pressure gas 18 is absent, attraction between magnets 17a and magnets 17b causes inner sleeve 10'' to return to the closed position (FIG. 21). It is contemplated that the location and/or polarity of magnets 17a and/or 17b may altered such that magnets 17a and magnets 17b repel each other to cause inner sleeve 10'' to return to the closed position.

Although the biasing members are illustrated as causing the inner sleeve to return to the closed position, it is contemplated that the biasing members may be structured to cause the inner sleeve to return to the open position. As will be discussed below in conjunction with FIGS. 22-24, a pressure reducing valve with a biasing member structured to cause the inner sleeve to return to the open position provides a flexing or dampening effect in the pressure curve. Although pressure reducing valve 1'''' is illustrated as employing permanent magnets, it is contemplated that electromagnets may be employed while remaining within the scope of the present invention. The use of electromagnets further reduces the amount of work required by a patient, allows increased control over the "flexing effect" or "dampening effect" (FIGS. 23-24), and, by altering the polarity of the electromagnets, allows a user to select whether the inner sleeve returns to an open position or to a closed position in the absence of a flow of positive pressure gas.

Figure 7:
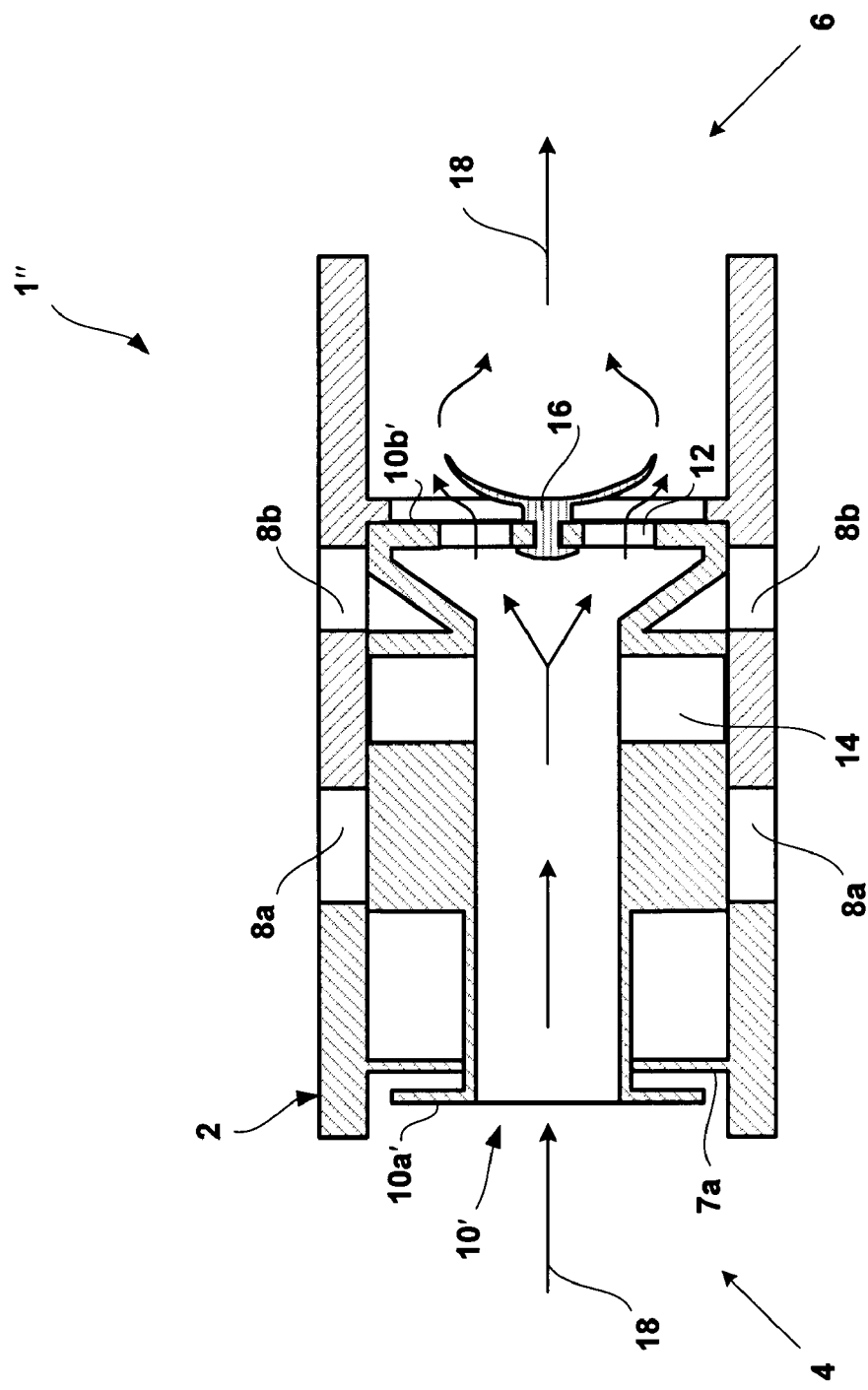
FIG. 7 is a schematic view of a pressure reducing valve illustrated in an open position according to yet another embodiment of the present invention.
Figure 8:
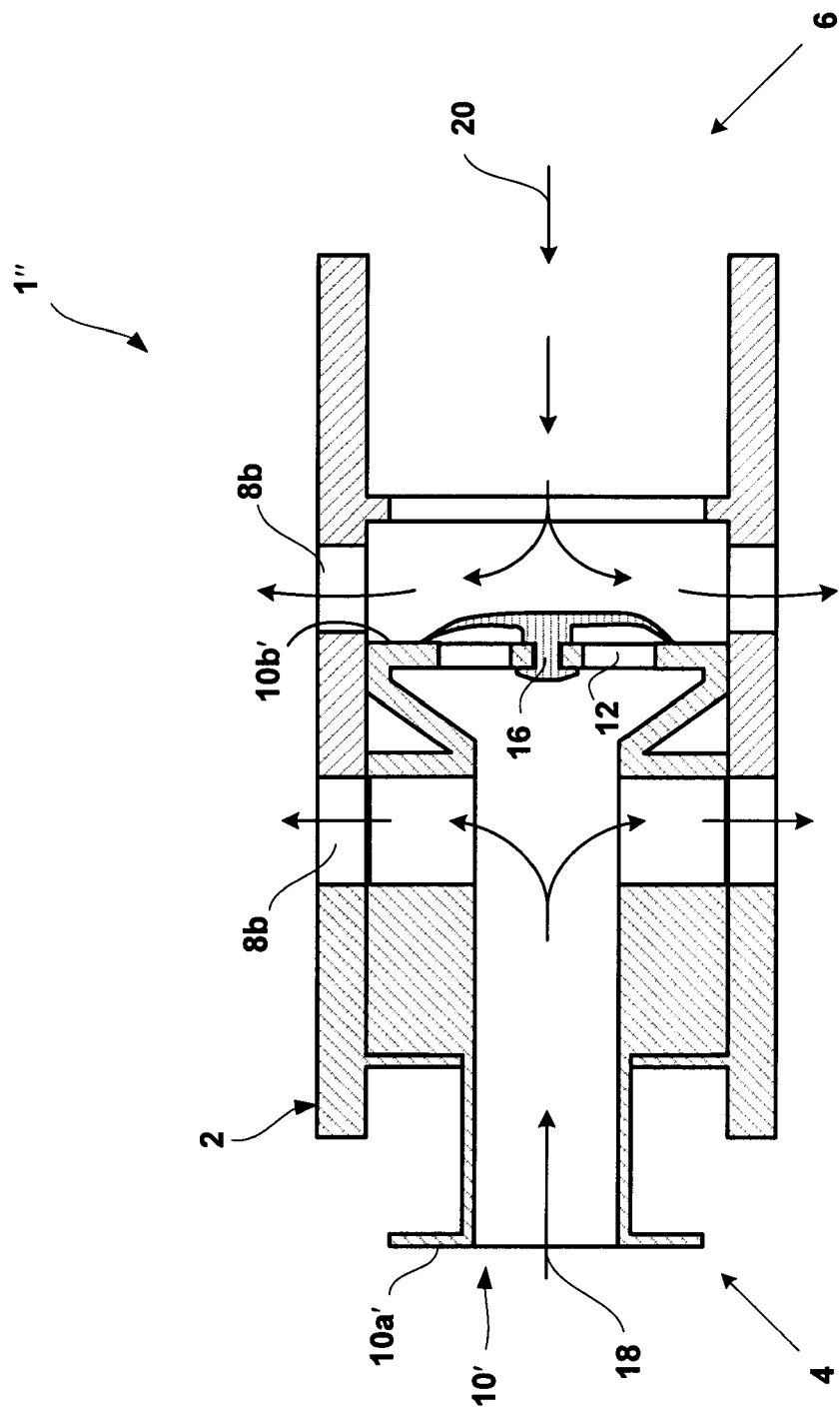
FIG. 8 illustrates the pressure reducing valve of FIG. 7 in a closed position.

A pressure reducing valve 1'' according to another embodiment of the present invention is illustrated in FIGS. 7-8. FIG. 7 illustrates pressure reducing valve 1'' in the open position. FIG. 8 illustrates pressure reducing valve 1'' in the closed position. Pressure reducing valve 1'' functions in a manner similar to that discussed above in conjunction with FIGS. 2-3 for pressure reducing valve 1.

In the embodiment shown in FIGS. 7 and 8, inner sleeve 10' has a pressure generator impingement face 10a' and a patient interface impingement face 10b' which are adapted to further decrease the amount of effort necessary to cause pressure reducing valve 1'' to be actuated to the closed position. Generally, a surface area of pressure generator impingement face 10a' is less than or equal to a surface area of patient interface impingement face 10b'. It is contemplated that the surface area of pressure generator impingement face 10a' is between approximately 75 percent and 100 percent of the surface area of patient interface impingement face 10b'; however, other percentages may be employed while remaining within the scope of the present invention.

In the current embodiment, for example, the surface area of pressure generator impingement face 10a' is approximately 95 percent of the surface area of patient interface impingement face 10b'. As a result, the total force applied to inner sleeve 10' at patient interface impingement face 10b' by flow of exhaust gas 20 is greater than the total force applied to inner sleeve 10' at pressure generator impingement face 10a' by flow of positive pressure gas 18. More specifically, when flow of exhaust gas 20 and flow of positive pressure gas 18 are at the same pressure, the inner sleeve 10' will move such that pressure reducing valve 1'' is actuated to the closed position because the force on the inner sleeve 10' at patient interface impingement face 10b' is greater than that at pressure generator impingement face 10a'. Accordingly, a patient is required to exert less effort during the expiratory phase to move inner sleeve 10' such that the pressure reducing valve 1'' is actuated to the closed position.

Figure 9:
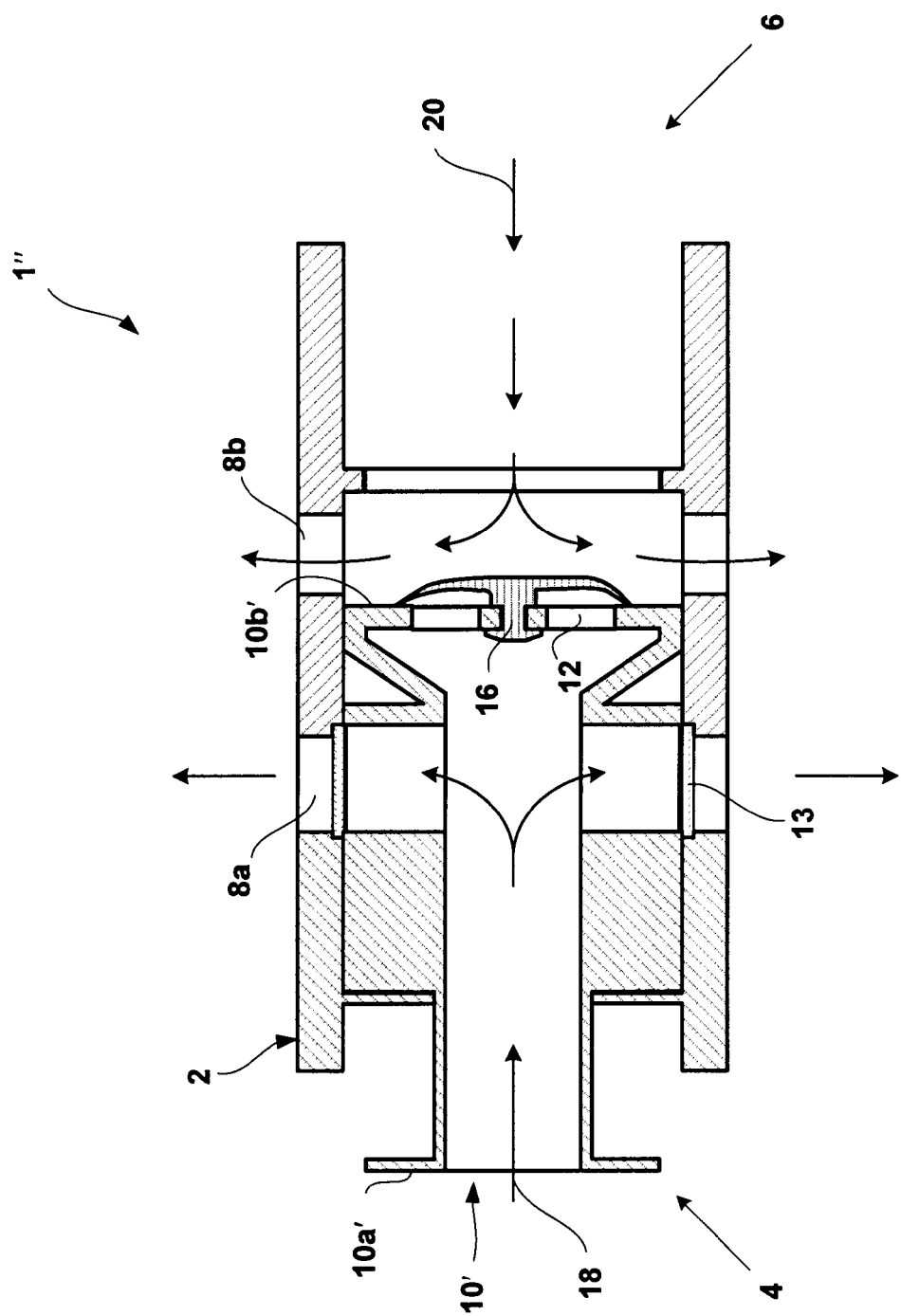
FIG. 9 is a schematic view of the pressure reducing valve of FIG. 7 with a sound muffling device according to one embodiment of the present invention.

FIG. 9 illustrates pressure reducing valve 1'' of FIGS. 7-8 with a muffler 13 associated with pressurized gas exhaust ports 8a. Muffler 13 is structured to reduce the noise caused by diverting flow of positive pressure gas 18 through pressurized gas exhaust ports 8a. In the current embodiment, for example, muffler 13 is structured to change flow of positive pressure gas 18 from a generally turbulent flow to a generally laminar flow. Although only illustrated as being associated with pressurized gas exhaust ports 8a of pressure reducing valve 1'', it is contemplated that muffler 13 may alternatively or additionally be associated with the pressurized gas ports 8a and/or with exhaust gas ports 8b of any pressure reducing valve of the present invention.

Figure 10:
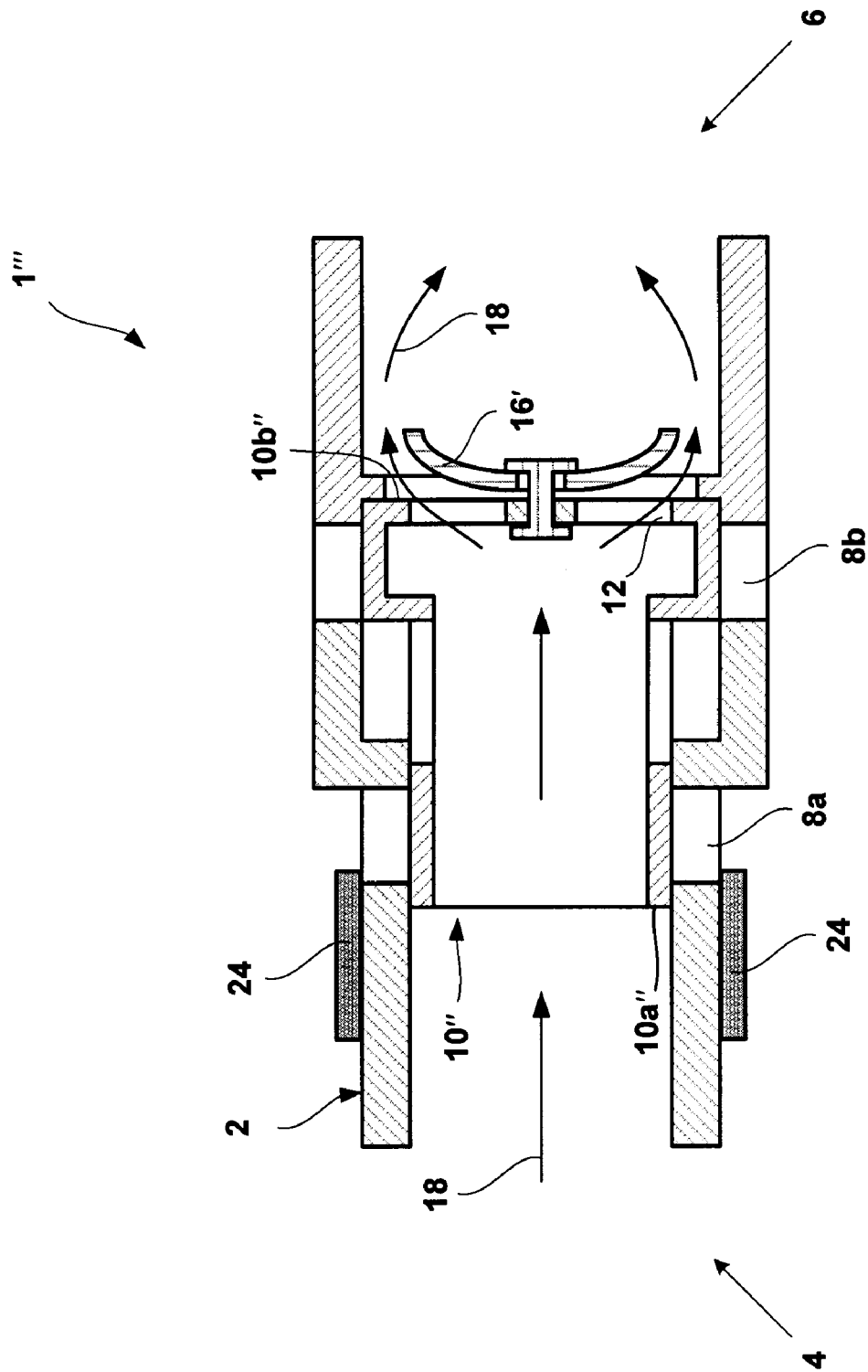
FIG. 10 is a schematic view of a pressure reducing valve illustrated in an open position according to yet another embodiment of the present invention.
Figure 11:
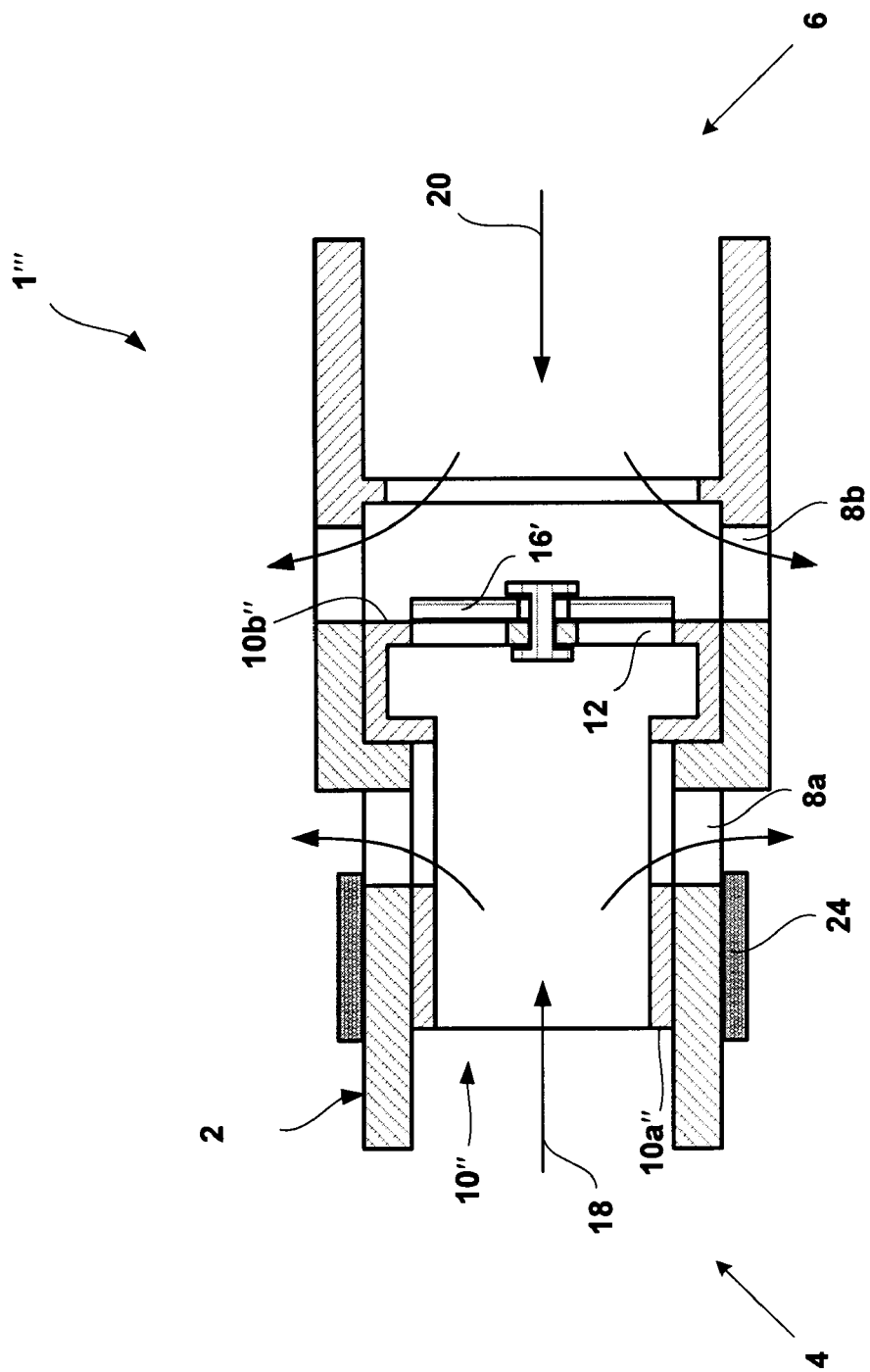
FIG. 11 illustrates the pressure reducing valve of FIG. 10 in a closed position.

A pressure reducing valve 1''' according to another embodiment is illustrated in FIGS. 10-11. FIG. 10 shows pressure reducing valve 1''' in the open position; whereas FIG. 11 shows pressure reducing valve 1''' in the closed position.

Pressure reducing valve 1''' functions in a manner similar to that discussed above in conjunction with FIGS. 7-8 for pressure reducing valve 1''. Inner sleeve 10'' has a pressure generator impingement face 10a'' and a patient interface impingement face 10b'' which are adapted to further decrease the amount of effort necessary to cause pressure reducing valve 11''' to be actuated to the closed position. Generally, a surface area of the pressure generator impingement face 10a'' is less than or equal to a surface area of the patient interface impingement face 10b''. It is contemplated that the surface area of the pressure generator impingement face 10a'' is between approximately 75 percent and 100 percent of the surface area of the patient interface impingement face 10b''; however, other percentages may be employed while remaining within the scope of the present invention. In the current embodiment, the surface area of the pressure generator impingement face 10a'' is approximately 95 percent of the surface area of the patient interface impingement face 10b''. Accordingly, a patient is required to exert less effort during the expiratory phase to move the inner sleeve 10'' such that pressure reducing valve 1''' is actuated to the closed position.

Pressure reducing valve 1''' includes an adjustable outer sleeve 24 which is movable along the outside of valve body 2. Adjustable outer sleeve 24 is adapted to occlude some portion of pressurized gas exhaust ports 8a. As a result the amount of flow of positive pressure gas 18 that is dumped through pressurized gas exhaust ports 8a can be controlled. By varying the flow of positive pressure gas 18 that is dumped, the expiratory positive air pressure (EPAP) can be adjusted. Accordingly, it is contemplated that a pressure reducing valve employing an adjustable outer sleeve 24 may be used for titration.

Although not shown in FIGS. 10-11, adjustable outer sleeve 24 may have a number of pre-determined set points, each related to a specific EPAP. For example, adjustable outer sleeve 24 may include a number of indentations which cooperate and/or engage with a rib on valve body 2. For instance, a first EPAP level is provided when a first indention engages the rib (e.g., adjustable outer sleeve 24 occludes a 5% of pressurized gas exhaust ports 8a); a second EPAP level is provided when a second indentation engages the rib (e.g., adjustable outer sleeve 24 occludes a 10% of pressurized gas exhaust ports 8*a*); etc. Additionally, although only illustrated as being associated with pressure reducing valve 1''' and pressure reducing valve 1'''', it is contemplated that adjustable outer sleeve 24 may alternatively or additionally be associated with any of the other pressure reducing valves of the present invention.

Figure 12:
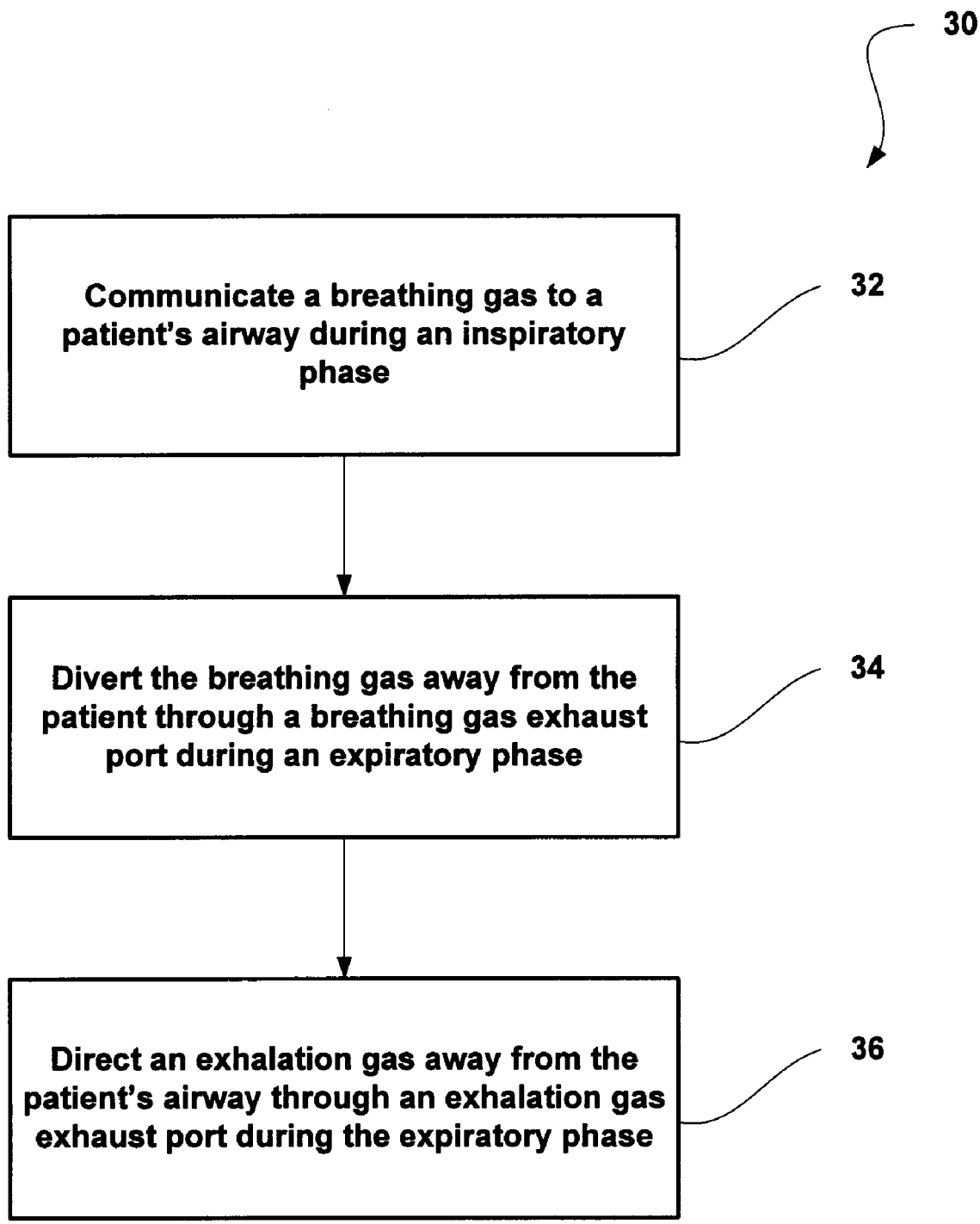
FIG. 12 illustrates an operational process for providing a breathing gas to a patient according to one embodiment of the present invention.

FIG. 12 illustrates an operational process 30 for providing a breathing gas to a patient. Operational process 30 begins with operation 32 in which, during an inspiratory phase, the breathing gas is communicated to the patient through a patient circuit having the breathing gas exhaust port and an exhalation gas exhaust port. In the current embodiment, flow of positive pressure gas 18 is communicated from pressure generating device 103 to the patient's airway through patient circuit 102 (FIG. 1). Patient circuit 102 includes a pressure reducing valve, for instance pressure reducing valve 1, which has pressurized gas exhaust ports 8*a* (i.e., which may also be referred to as the breathing gas exhaust port) and exhalation gas exhaust ports 8*b*. As discussed above, pressure reducing valve 1 is in the open position during the inspiratory phase, thus allowing flow of positive pressure gas 18 to be communicated through inner ports 12 to the patient's airway. Additionally, pressurized gas exhaust ports 8*a* and exhalation gas exhaust ports 8*b* are blocked by inner sleeve 10 during the inspiratory phase.

Operational control is then passed to operation 34 where, during the expiratory phase, the breathing gas is diverted away from the airway of such a patient through the breathing gas exhaust port. In the current embodiment, pressure reducing valve 1 is in the closed position during the expiratory phase. In the closed position, sealing member 16 blocks flow of positive pressure gas 18 from communication with the patient's airway. Flow of positive pressure gas 18 is diverted through orifices 14 to pressurized gas exhaust ports 8*a* where, in the current embodiment, flow of positive pressure gas 18 is dumped to atmosphere.

In operation 36, the exhalation gas from the airway of the patient is directed through the exhalation gas exhaust port during the expiratory phase. As stated above in conjunction with operation 34, pressure reducing valve 1 is in the closed position during the expiratory phase. Sealing member 16 prevents flow of exhalation gas 20 from passing through inner ports 12. Instead, flow of exhalation gas 20 is directed through exhalation gas exhaust ports 8*b* where, in the current embodiment, it is dumped to atmosphere. It should be noted that during the expiratory phase, flow of exhalation gas 20 and flow of positive pressure gas 18 are substantially isolated from each other by sealing member 16 such that the effort required by the patient to exhale is reduced.

Figure 13:
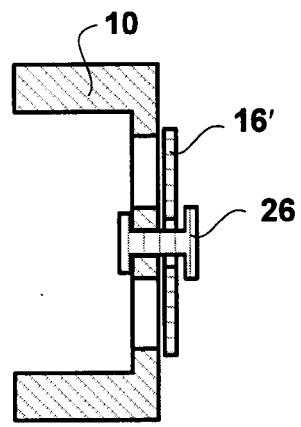
FIGS. 13-19b illustrate various sealing member arrangements for a pressure reducing valve according to the present invention.

The pressure reducing valves illustrated in FIGS. 2-9 employ an umbrella valve 16 as a sealing member. FIGS. 13-19*b* illustrate several alternative arrangements for sealing member 16 which may be used for the pressure reducing valves of the present invention. FIG. 13, for example, illustrates a diaphragm valve 16' coupled to inner sleeve 10 by a valve stem 26 which is inserted into inner sleeve 10 according to one embodiment of the present invention.

Figure 14:
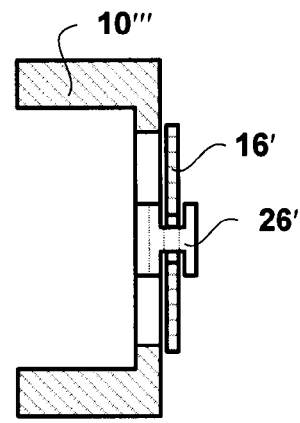

FIG. 14 shows diaphragm valve 16' coupled to inner sleeve 10''' by a valve stem 26' which is an integral part of inner sleeve 10''' according to one embodiment of the present invention.

Figure 15A:
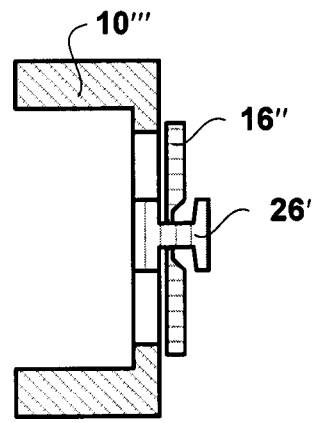
Figure 15B:
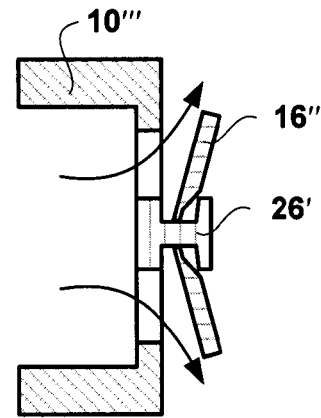

FIGS. 15*a* and 15*b* illustrate a butterfly valve 16'' coupled to inner sleeve 10''' by a valve stem 26' according to one embodiment of the present invention. FIG. 15*a* shows the butterfly valve 16'' in the closed position, whereas FIG. 15*b* shows the butterfly valve 16'' in the open position.

Figure 16A:
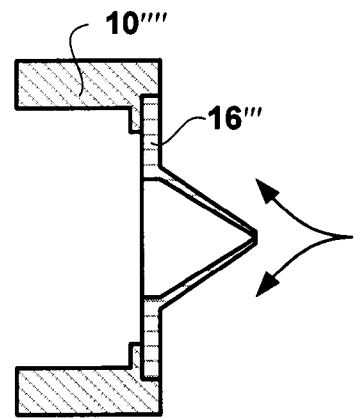
Figure 16B:
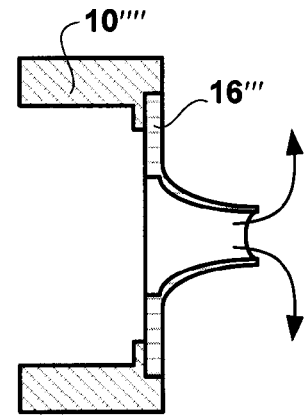

FIGS. 16*a* and 16*b* illustrate a duck-bill valve 16''' coupled to an inner sleeve 10'''' according to one embodiment of the present invention. FIG. 16*a* shows the duck-bill valve 16''' in the closed position, whereas FIG. 16*b* shows the duck-bill valve 16''' in the open position.

Figure 17A:
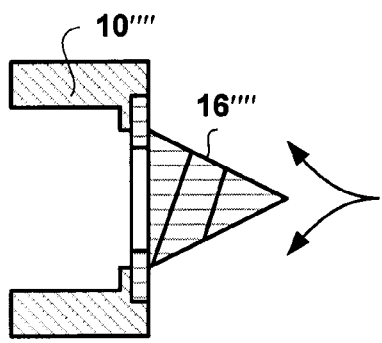
Figure 17B:
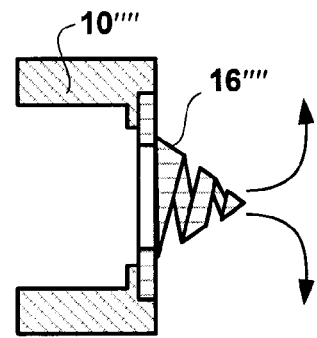

FIGS. 17*a* and 17*b* illustrate a cone valve 16'''' coupled to an inner sleeve 10'''' according to one embodiment of the present invention. FIG. 17*a* shows the cone valve 16'''' in the closed position, whereas FIG. 17*b* shows the cone valve 16'''' in the open position.

Figure 18A:
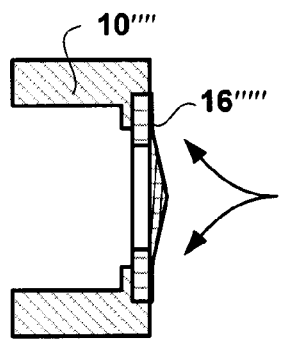
Figure 18B:
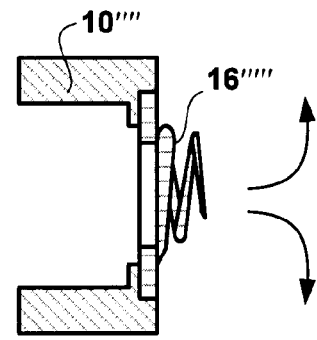

FIGS. 18*a* and 18*b* illustrate a spiral valve 16''''' coupled to an inner sleeve 10'''' according to one embodiment of the present invention. FIG. 18*a* shows the spiral valve 16''''' in the closed position, whereas FIG. 18*b* shows the spiral valve 16''''' in the open position.

Figure 19A:
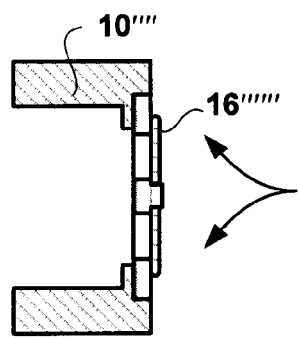
Figure 19B:
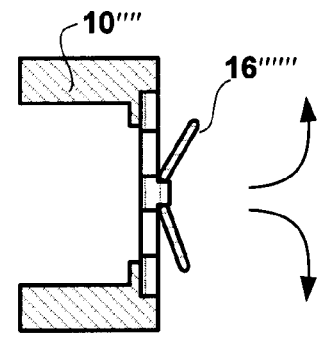

FIGS. 19*a* and 19*b* illustrate a bi-leaflet valve 16'''''' coupled to an inner sleeve 10'''' according to one embodiment of the present invention. FIG. 19*a* shows the bi-leaflet valve 16'''''' in the closed position, whereas FIG. 19*b* shows the bi-leaflet valve 16'''''' in the open position.

Although several arrangements for the sealing member have been discussed herein, it is contemplated that other arrangements may be employed while remaining within the scope of the present invention.

Figure 22:
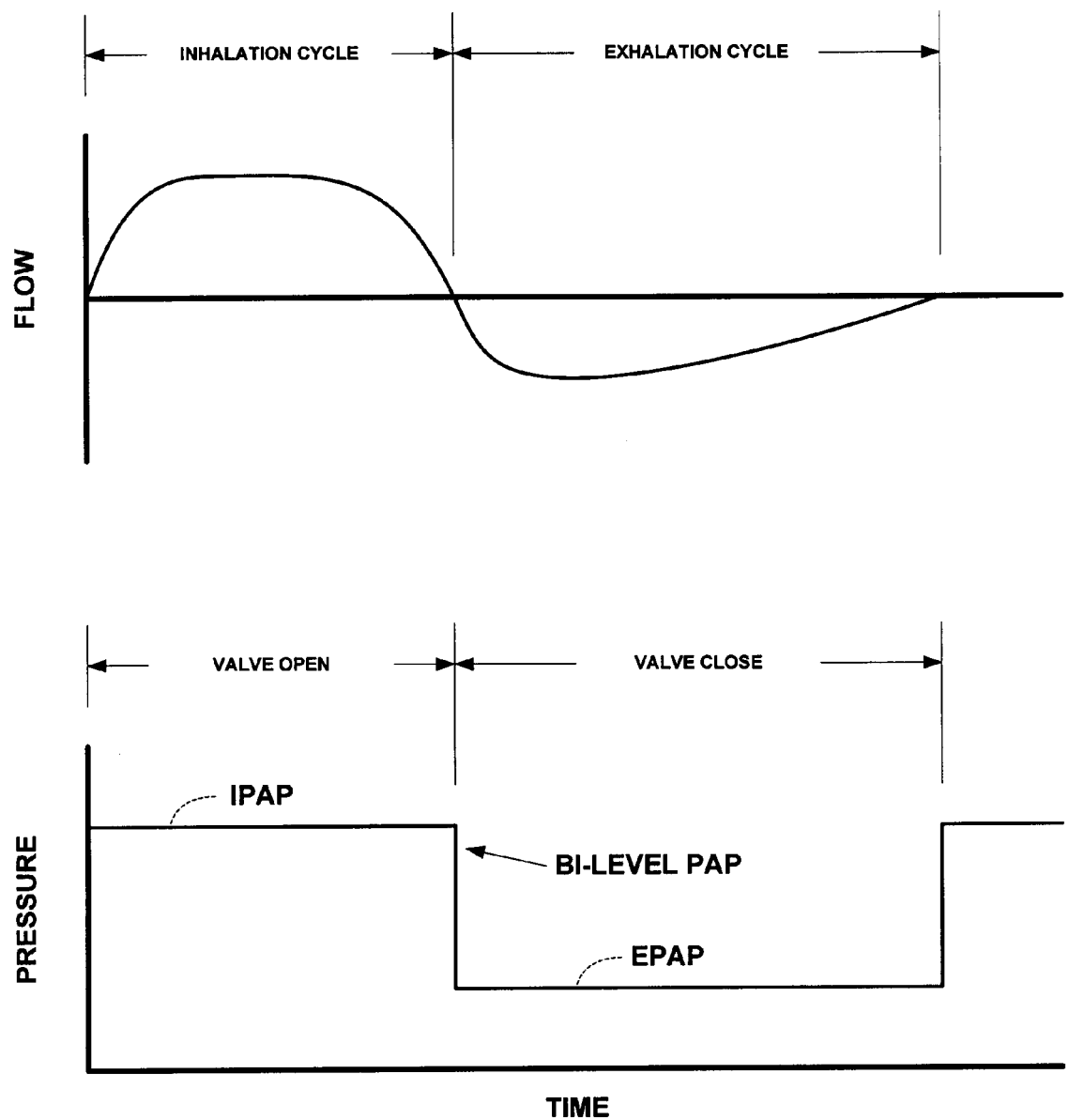
FIGS. 22-24 are various flow/pressure curves illustrating the operation of the pressure reducing valves of the present invention.
Figure 23:
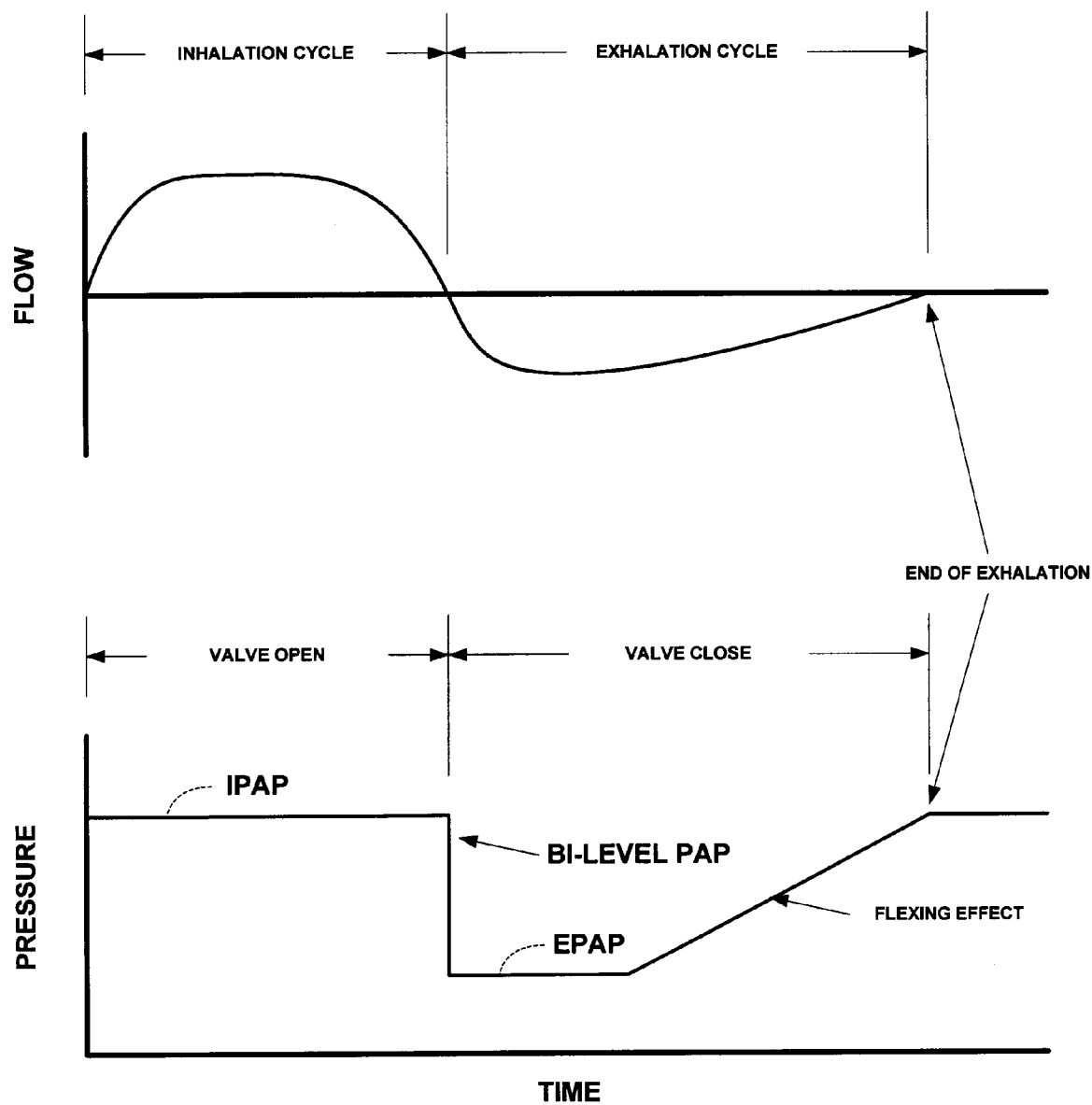
Figure 24:
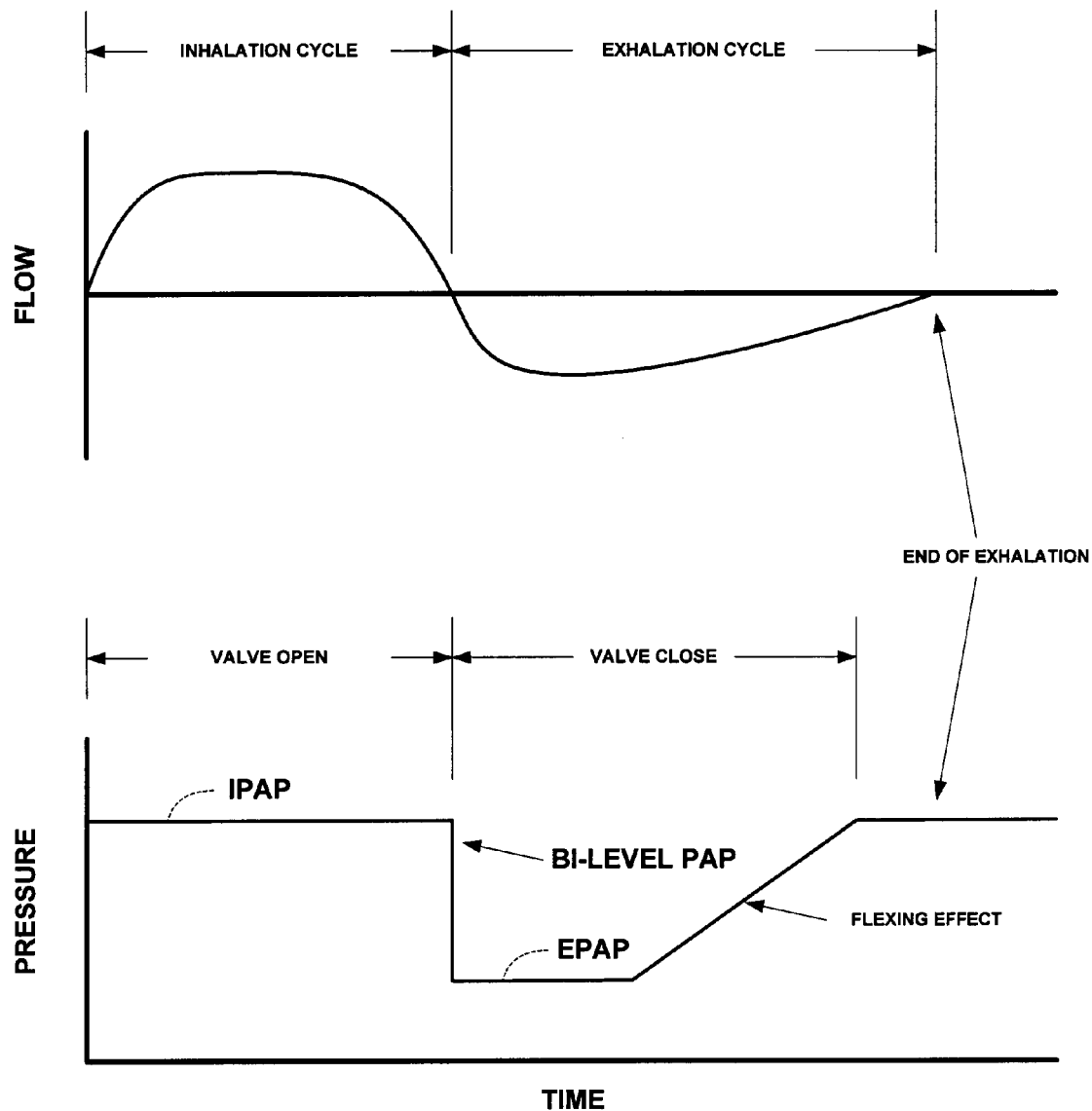

FIGS. 22-24 illustrated flow and pressure curves output by pressure reducing valves of the present invention when, for example, used in system 100 (FIG. 1) with the pressure generating device 103 producing a flow of gas at a constant positive pressure. Although discussed in conjunction with a CPAP pressure generating device 103 (which produces the flow of gas at a constant positive pressure), it is contemplated that other types of pressure generating devices may be employed. The bi-level PAP curves illustrated in FIGS. 22-24 are generated by pressure reducing valves of the present invention.

Referring to FIG. 22, when the pressure reducing valve is open, the inspiratory positive air pressure is equal to the constant positive air pressure (i.e., IPAP=CPAP) produced by the pressure generating device 103. When the pressure reducing valve is closed, the expiratory positive air pressure is less than the constant positive air pressure (i.e., EPAP<CPAP) because the flow of positive pressure gas is dumped through pressurized gas exhaust ports 8*a*. The expiratory positive air pressure level is dependent upon, among others, the size of pressurized gas exhaust ports 8*a* (and thus the amount of flow of positive pressure gas 18 that can be dumped).

FIGS. 23 and 24 illustrates flow and a pressure curves corresponding to the output of pressure reducing valves having a biasing member structured to cause the inner sleeve to return to the open position. As seen in FIGS. 23 and 24, the biasing member urges the inner sleeve to move to the open position prior to the end of the exhalation cycle; thus providing a flexing or dampening effect during exhalation. As seen in FIG. 23, the biasing member causes the pressure reducing valve to close at the end of the exhalation cycle; whereas in FIG. 24, the biasing member causes the pressure reducing valve to close prior to the end of the exhalation period.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

For example, although the pressure reducing valves illustrated in the embodiments herein have separate ports within the wall of valve body 2, the terms "pressurized gas exhaust ports" and "exhalation gas exhaust ports" are contemplated to encompass a single port in the valve body 2 that is divided by inner sleeve 10 in such a manner as to prevent flow of positive pressure gas 18 from mixing with flow of exhalation gas 20. As another example, it is to be understood that the present invention contemplates that, to the extent possible, one or more features of any embodiment can be combined with one or more features of any other embodiment.

What is claimed is:

1. A pressure reducing valve, comprising:
a valve body having a number of pressurized gas exhaust ports and a number of exhalation gas exhaust ports; and
an inner sleeve having a number of inner ports, wherein the inner sleeve is movable within the valve body between a closed position in which the inner ports are closed and the pressurized gas exhaust ports and the exhalation gas exhaust ports are open and an open position in which the inner ports are open and the pressurized gas exhaust ports and the exhalation gas exhaust ports are closed, wherein the pressurized gas exhaust ports are structured to operatively communicate a flow of positive pressure gas provided to the pressure reducing valve through the valve body to atmosphere when the inner sleeve is in the closed position and wherein the exhalation gas exhaust ports are structured to operatively communicate a flow of exhalation gas provided to the pressure reducing valve through the valve body to atmosphere when the inner sleeve is in the closed position in a manner wherein no more than a negligible amount of mixing of the flow of positive pressure gas and the flow of exhalation gas will occur.

2. The pressure reducing valve of claim 1, wherein the valve body includes a pressure generator end and a patient interface end, wherein the pressure generator end is structured to receive the flow of positive pressure gas from a pressure generating device, and wherein the patient interface end is structured to deliver the flow of positive pressure gas to a patient and receive the flow of exhalation gas from such a patient.

3. The pressure reducing valve of claim 2,
wherein the inner sleeve has a number of orifices which are in fluid communication with the number of pressurized gas exhaust ports when the inner sleeve is in the closed position, and
wherein the inner sleeve has associated therewith a sealing member structured to close the inner ports and hinder the flow of positive pressure gas from the pressure generator end to the patient interface end when the inner sleeve is in the closed position and structured to allow the flow of positive pressure gas from the pressure generator end to the patient interface end when the inner sleeve is in the open position,
the sealing member being one of a diaphragm valve, a butterfly valve, a duck-bill valve, an umbrella valve, a cone valve, a spiral valve, and a bi-leaflet valve.

4. The pressure reducing valve of claim 2, further comprising a biasing member for returning the inner sleeve to one of the closed position and the open position when the flow of positive pressure gas is absent from the pressure generator end.

5. The pressure reducing valve of claim 1, wherein the inner sleeve has a pressure generator impingement face and a patient interface impingement face, and wherein a surface area of the pressure generator impingement face is between approximately 75 percent and 100 percent of a surface area of the patient interface impingement face.

6. The pressure reducing valve of claim 1, further comprising at least one of
a muffler associated with at least one of the pressurized gas exhaust ports and the exhalation gas exhaust ports, and
an adjustable outer sleeve structured to control an amount of gas discharged through one of the pressurized gas exhaust ports and the exhalation gas exhaust ports.

7. The pressure reducing valve of claim 1, wherein the inner sleeve has a pressure generator impingement face and a patient interface impingement face, and wherein a surface area of the pressure generator impingement face is less than a surface area of the patient interface impingement face such that when the flow of positive pressure gas and the flow of exhalation gas are at the same pressure, the inner sleeve will be actuated to the closed position.

8. A pressure reducing valve, comprising:
a valve body having a patient interface end and a pressure generator end with at least two exhaust ports therebetween, wherein a first one of the at least two exhaust ports is fluidly coupled through the valve body to atmosphere and wherein a second one of the at least two exhaust ports is fluidly coupled through the valve body to atmosphere; and
an inner sleeve movable within the valve body, wherein the inner sleeve is structured to communicate a flow of positive pressure gas from the pressure generator end to the patient interface end during an inspiratory phase, and wherein the inner sleeve is structured to divert the flow of positive pressure gas to the first one of the at least two exhaust ports and through the valve body to atmosphere and to communicate a flow of exhalation gas from the patient interface end to the second one of the at least two exhaust ports and through the valve body to atmosphere during the expiratory phase in a manner wherein no more than a negligible amount of mixing of the flow of positive pressure gas and the flow of exhalation gas will occur.

9. The pressure reducing valve of claim 8, wherein the pressure generator end is structured to couple with a gas generator operable to produce the flow of positive pressure gas, and wherein the patient interface end is structured to couple with a patient interface device operable to deliver the flow of positive pressure gas to a patient's airway and operable to receive a flow of exhalation gas from such a patient's airway.

10. The pressure reducing valve of claim 8,
wherein the inner sleeve has a number of inner ports operable to communicate the flow of positive pressure gas from the pressure generator end to the patient interface end during inhalation, and
wherein the inner sleeve has associated therewith a sealing member structured to hinder communication of the flow of positive pressure gas from the pressure generator end to the patient interface end through at least some of the number of inner ports during exhalation.

11. The pressure reducing valve of claim 10, wherein the inner sleeve has a pressure generator impingement face and a patient interface impingement face, and wherein a surface area of the pressure generator impingement face is less than a surface area of the patient interface impingement face such that when the flow of positive pressure gas and the flow of exhalation gas are at the same pressure, the inner sleeve will be actuated to a closed position wherein the inner ports are closed and the at least two exhaust ports are open.

12. The pressure reducing valve of claim 8, further comprising a biasing means for returning the inner sleeve to a position in which a flow of exhalation gas is delivered to the second one of the at least two exhaust ports when the flow of positive pressure gas is absent from the pressure generator end.

13. The pressure reducing valve of claim 8 further comprising at least one of
    a muffler associated with at least one of the at least two exhaust ports; and
    an adjustable outer sleeve structured to control an amount of gas discharged through at least one of the two exhaust ports, wherein the adjustable outer sleeve is adapted for auto-titrating a patient.

14. A method for providing a breathing gas to a patient, comprising:
    communicating the breathing gas through a patient circuit to an airway of such a patient during an inspiratory phase, wherein the patient circuit has at least a breathing gas exhaust port and an exhalation gas exhaust port;
    diverting the breathing gas away from the airway of such a patient through the breathing gas exhaust port to atmosphere during an expiratory phase; and
    directing an exhalation gas from the airway of such a patient through the exhalation gas exhaust port to atmosphere during the expiratory phase, wherein during the expiratory phase no more than a negligible amount of mixing the breathing gas and the exhalation gas is permitted occur.

15. The method of claim 14, wherein communicating the breathing gas through a patient circuit comprises delivering the breathing gas to the airway of such a patient via a pressure reducing valve having a valve body and an inner sleeve, wherein the valve body includes the breathing gas exhaust port and the exhalation gas exhaust port therein, wherein the inner sleeve has a number of inner ports and a number of orifices, and wherein the inner sleeve is positioned to an open position.

16. The method of claim 15 wherein said pressure reducing valve has an adjustable outer sleeve and wherein the method further comprises controlling the adjustable outer sleeve to titrate such a patient.

17. The method of claim 15,
    wherein diverting the breathing gas away from the airway of such a patient comprises positioning the inner sleeve to a closed position and redirecting the breathing gas to the breathing gas exhaust port and out to atmosphere through the breathing gas exhaust port, and
    wherein directing the exhalation gas away from the airway of such a patient comprises positioning the inner sleeve to the closed position and directing the exhalation gas to the exhalation gas exhaust port and out to atmosphere through the exhalation gas exhaust port.

18. The method of claim 17, wherein the inner sleeve has a pressure generator impingement face and a patient interface impingement face, and wherein a surface area of the pressure generator impingement face is less than a surface area of the patient interface impingement face such that when the flow of breathing gas and the flow of exhalation gas are at the same pressure, the inner sleeve will be actuated to the closed position.

19. In a system adapted to provide a regimen of respiratory therapy to a patient, the system including a patient circuit with a pressure reducing valve having a first exhaust port and a second exhaust port therein, a method, comprising: delivering the flow of breathing gas to the airway of such a patient through the patient circuit during an inspiratory phase; and
    diverting the flow of breathing gas away from the airway of such a patient through the first exhaust port to atmosphere while disposing of a flow of exhalation gas from the airway of such a patient through the second exhaust port to atmosphere during an exhalation phase in a manner wherein no more than a negligible amount of mixing of the flow of breathing gas and the flow of exhalation gas is permitted occur,
    wherein the pressure reducing valve has a valve body and an inner sleeve, wherein delivering the flow of breathing gas includes employing the flow of breathing gas to move the inner sleeve within the valve body to an open position, and
    wherein diverting the flow of breathing gas while disposing of the flow of exhalation gas includes employing the flow of exhalation gas to move the inner sleeve within the valve body to a closed position.

20. The method of claim 19 wherein diverting the flow of breathing gas while disposing of the flow of exhalation gas further comprises muffling sound produced by at least one of the flow of breathing gas exiting the first exhaust port and the flow of exhalation gas exiting the second exhaust port.

21. The method of claim 19 wherein the pressure reducing valve has an adjustable outer sleeve, the method further comprising controlling at least one of an amount of breathing gas diverted through the first exhaust port and an amount of exhalation gas directed though the second gas exhaust port.

22. The method of claim 19, wherein the inner sleeve has a pressure generator impingement face and a patient interface impingement face, and wherein a surface area of the pressure generator impingement face is less than a surface area of the patient interface impingement face such that when the flow of breathing gas and the flow of exhalation gas are at the same pressure, the inner sleeve will be actuated to the closed position.

23. An apparatus for delivering a flow of positive pressure gas to an airway of a patient, the apparatus comprising:
    a gas flow generator structured to produce the flow of positive pressure gas;
    a patient interface device structured to communicate the flow of positive pressure gas to the airway of such a patient; and
    a patient circuit structured to couple the gas flow generator to the patient interface device, wherein the patient circuit includes a pressure reducing valve with a valve body and an inner sleeve, wherein the valve body has at least two exhaust ports therein, wherein a first one of the at least two exhaust ports is fluidly coupled through the valve body to atmosphere and wherein a second one of the at least two exhaust ports is fluidly coupled through the valve body to atmosphere, wherein the inner sleeve is movable within the valve body, wherein the inner sleeve is structured to communicate the flow of positive pressure gas from the gas flow generator to the patient interface device during an inspiratory phase, and wherein the inner sleeve is structured to divert the flow of positive pressure gas to the first one of the at least two exhaust ports and through the valve body to atmosphere and to communicate a flow of exhalation gas from the airway of such a patient to the second one of the at least two exhaust ports and through the valve body to atmosphere during an expiratory phase in a manner wherein no more than a negligible amount of mixing of the flow of positive pressure gas and the flow of exhalation gas will occur.

24. The apparatus of claim 23, wherein the pressure reducing valve further comprises a biasing means structured to locate the inner sleeve to a position in which the flow of exhalation gas is delivered to the second one of the at least two exhaust ports when the flow of positive pressure gas is absent.

25. The apparatus of claim 23, wherein the inner sleeve has a number of inner ports operable to communicate the flow of positive pressure gas from the gas flow generator to the patient interface device during inhalation, and wherein the apparatus further comprises a sealing member structured to hinder communication of the flow of positive pressure gas from the gas flow generator to the patient interface device through at least some of the number of inner ports to during exhalation.

26. The apparatus of claim 23 further comprising an adjustable outer sleeve structured to control an amount of gas discharged through at least one of the two exhaust ports, wherein the adjustable outer sleeve is adapted for titration of a patient.

27. The apparatus of claim 23, wherein the inner sleeve has a pressure generator impingement face and a patient interface impingement face, and wherein a surface area of the pressure generator impingement face is between approximately 75 percent and 100 percent of a surface area of the patient interface impingement face.

28. The apparatus of claim 23, wherein the inner sleeve has a pressure generator impingement face and a patient interface impingement face, and wherein a surface area of the pressure generator impingement face is less than a surface area of the patient interface impingement face such that when the flow of positive pressure gas and the flow of exhalation gas are at the same pressure, the inner sleeve will be actuated to a closed position wherein the inner ports are closed and the at least two exhaust ports are open.

* * * * *